US012594088B2

(12) United States Patent
Deck et al.

(10) Patent No.: US 12,594,088 B2
(45) Date of Patent: Apr. 7, 2026

(54) UNCLAMPED FIRING LOCKOUT FOR LINEAR SURGICAL STAPLER

(71) Applicant: Cilag GmbH International, Zug (CH)

(72) Inventors: Andrew C. Deck, Cincinnati, OH (US); Jason D. Jones, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/502,464

(22) Filed: Nov. 6, 2023

(65) Prior Publication Data

US 2025/0143734 A1     May 8, 2025

(51) Int. Cl.
*A61B 17/28* (2006.01)
*A61B 17/072* (2006.01)

(52) U.S. Cl.
CPC ...... *A61B 17/2833* (2013.01); *A61B 2017/07257* (2013.01); *A61B 2017/07271* (2013.01)

(58) Field of Classification Search
CPC ...... A61B 17/2833; A61B 2017/07257; A61B 2017/07271
See application file for complete search history.

(56) References Cited

U.S. PATENT DOCUMENTS

| | | | | |
|---|---|---|---|---|
| 4,869,415 A | * | 9/1989 | Fox | A61B 17/07207 |
| | | | | 227/19 |
| 5,065,929 A | * | 11/1991 | Schulze | A61B 17/07207 |
| | | | | 227/19 |

| | | | | |
|---|---|---|---|---|
| 5,489,058 A | * | 2/1996 | Plyley | A61B 17/07207 |
| | | | | 227/176.1 |
| 5,673,842 A | * | 10/1997 | Bittner | A61B 17/07207 |
| | | | | 227/180.1 |
| 5,893,506 A | | 4/1999 | Powell | |
| 10,631,866 B2 | | 4/2020 | Laurent et al. | |
| 10,667,818 B2 | * | 6/2020 | McLain | A61B 17/3205 |
| 10,687,819 B2 | | 6/2020 | Stokes et al. | |
| 10,874,398 B2 | | 12/2020 | Baxter, III et al. | |
| 10,898,187 B2 | * | 1/2021 | Deck | A61B 17/072 |
| 10,898,197 B2 | | 1/2021 | Baxter, III et al. | |
| 10,905,419 B2 | | 2/2021 | Schings et al. | |
| 10,932,781 B2 | | 3/2021 | Jones et al. | |
| 11,033,266 B2 | | 6/2021 | Jones et al. | |
| 11,045,193 B2 | | 6/2021 | Schings et al. | |
| 11,219,454 B2 | | 1/2022 | Schings et al. | |
| 11,224,425 B2 | | 1/2022 | Schings | |
| 11,229,433 B2 | * | 1/2022 | Schings | A61B 17/0644 |
| 11,278,285 B2 | | 3/2022 | Deck et al. | |

(Continued)

OTHER PUBLICATIONS

Design U.S. Appl. No. 29/842,580, filed Jun. 14, 2022, by Schings, et al., entitled: "Staple Cartridge for a Linear Surgical Stapler.".

(Continued)

*Primary Examiner* — Thomas M Wittenschlaeger
(74) *Attorney, Agent, or Firm* — FBT Gibbons LLP

(57) ABSTRACT

An apparatus includes a first and second elongate member that can releasably couple together to in order to cooperate to clamp and staple tissue, a clamp lever and latch body that together can latch the first and second elongate member to clamp tissue, a firing assembly that can sever and staple clamped tissue, and a lockout assembly that can prevent firing of the firing assembly until the clamp leer and latch body successfully latch the first and second elongate member together to clamp tissue.

18 Claims, 22 Drawing Sheets

(56) References Cited

U.S. PATENT DOCUMENTS

| | | | |
|---|---|---|---|
| 11,399,827 B2 | 8/2022 | Schings | |
| 11,937,812 B2 | 3/2024 | Schings et al. | |
| 12,016,555 B2 | 6/2024 | Wang | |
| 2011/0253766 A1* | 10/2011 | Baxter, III | A61B 17/07207 |
| | | | 227/176.1 |
| 2020/0046353 A1* | 2/2020 | Deck | A61B 17/07207 |
| 2020/0113562 A1* | 4/2020 | Schings | A61B 17/1114 |

OTHER PUBLICATIONS

Design U.S. Appl. No. 29/842,581, filed Jun. 14, 2022, by Deck et al., entitled: "Linear Surgical Stapler.".
International Search Report and Written Opinion dated Feb. 18, 2025, for International Application No. PCT/IB2024/060984, 15 pages.

* cited by examiner

UNCLAMPED FIRING LOCKOUT FOR LINEAR SURGICAL STAPLER

BACKGROUND

In some surgical operations, such as a gastrointestinal anastomosis, it may be desirable to clamp down on one or more layers of tissue, cut through the clamped layers, and simultaneously drive staples through the layers to substantially seal the severed layers together near their severed ends. One such instrument that may be used in such operations is a linear surgical stapler, also referred to as a "linear cutter." A linear surgical stapler generally includes a first half (referred to as a "cartridge half" or "reload half") having a distal jaw configured to support a staple cartridge (or "reload"), and a second half (referred to as an "anvil half") having a distal jaw that supports an anvil surface having staple forming features. The stapler further includes a moveable clamp lever configured to releasably clamp the stapler halves together. The stapler halves are configured to releasably couple together and pivot relative to one another to clamp tissue positioned between the two distal jaws when the clamp lever is closed. A firing assembly of the stapler is configured to be actuated to cut the clamped layers and simultaneously drive staples through the tissue on either side of the cut line. After the stapler is fired, the clamp lever may be opened, and the stapler halves separated to release the severed and stapled tissue.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
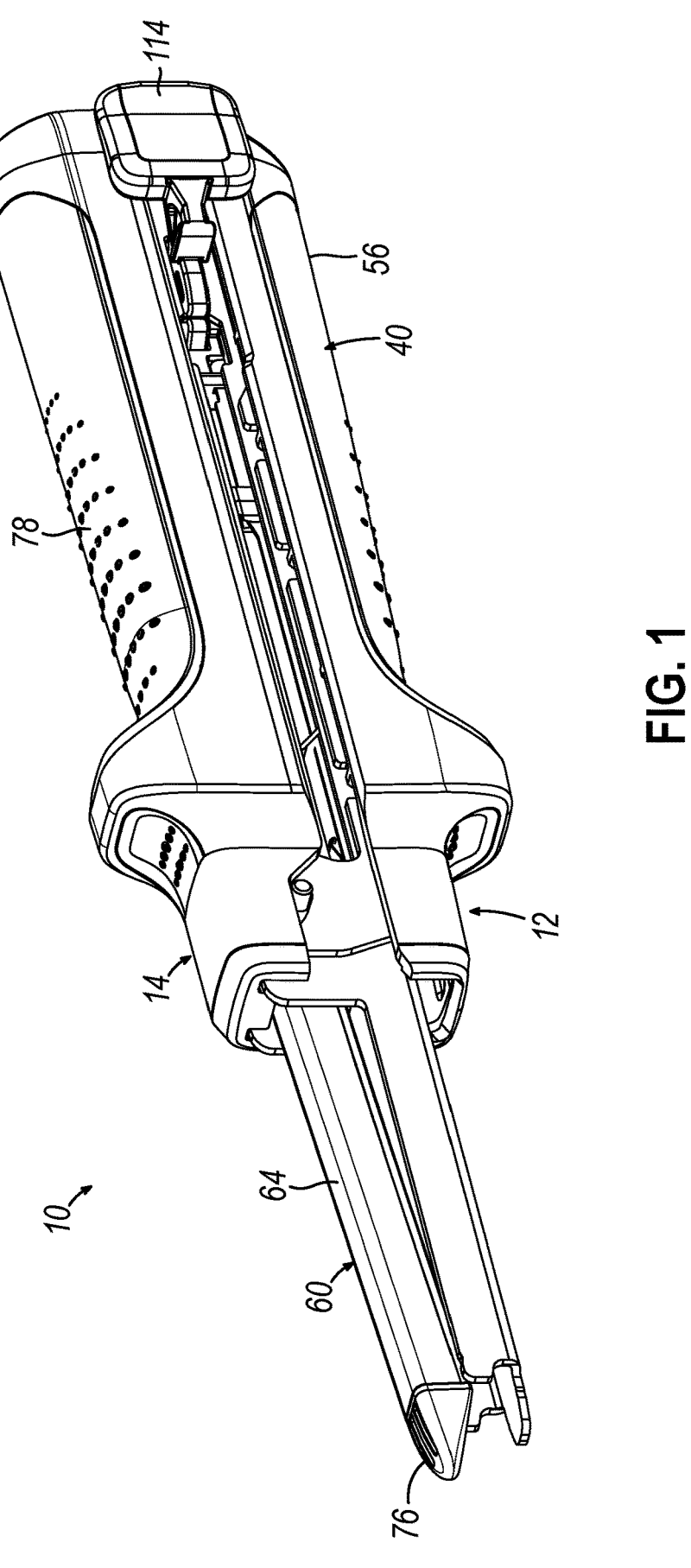
FIG. 1 depicts a perspective view of an illustrative linear surgical stapler, showing a cartridge half and an anvil half of the stapler coupled together with a clamp lever of the cartridge half in a fully closed position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for illustrative description purposes only and are not intended to be limiting or absolute. In that regard, it will be understood that surgical instruments such as those disclosed herein may be used in a variety of orientations and positions not limited to those shown and described herein.

Furthermore, the terms "about" and "approximately" as used herein in connection with any numerical values or ranges indicate a suitable dimensional tolerance that allows the referenced feature(s) to function for its intended purpose as described herein.

I. Illustrative Linear Surgical Staplers

A. Overview of Linear Surgical Stapler

Figure 2:
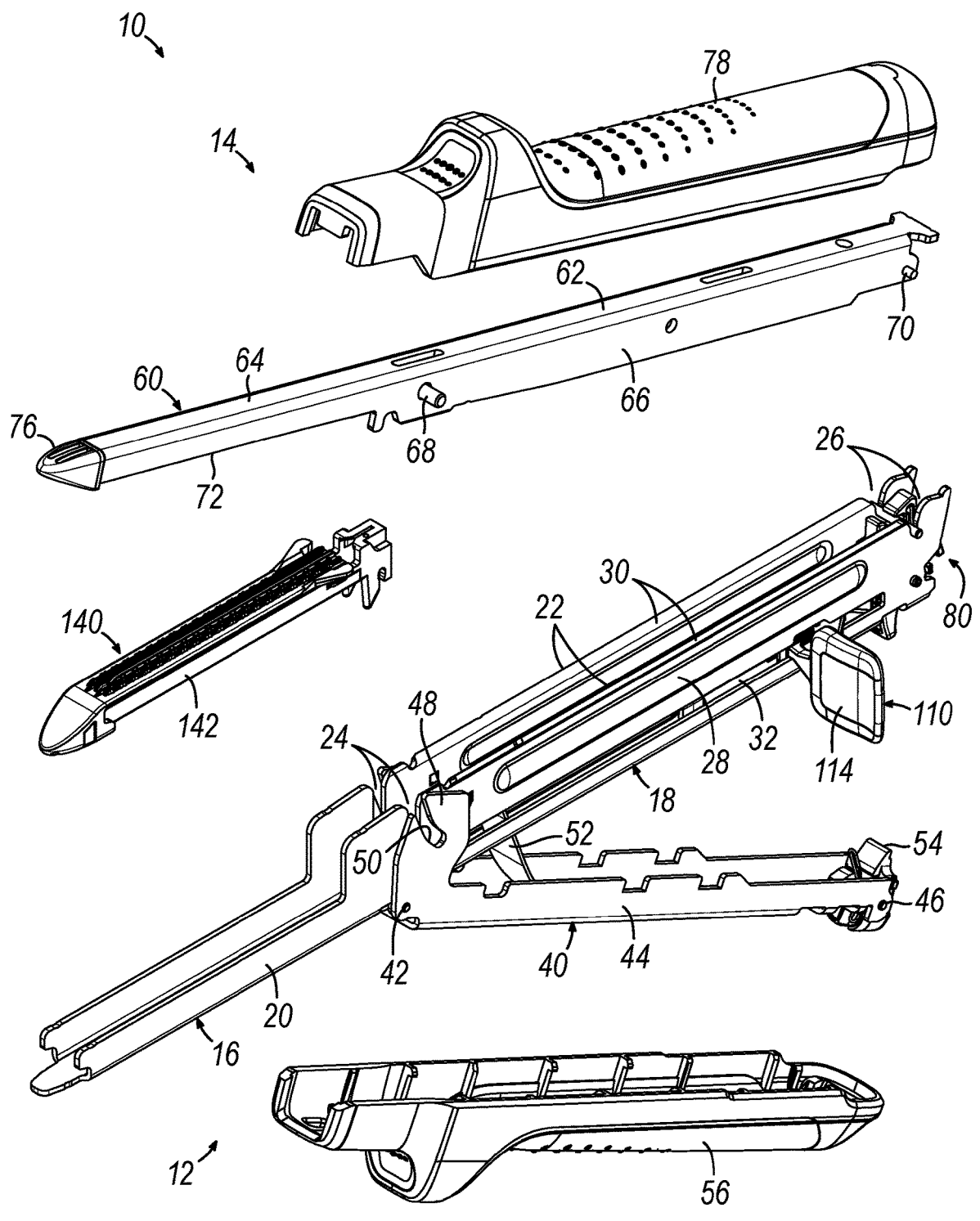
FIG. 2 depicts an exploded perspective view of the linear surgical stapler of FIG. 1, additionally showing a staple cartridge.

FIGS. 1-2 show an illustrative linear surgical stapler (10) (also referred to as a "linear cutter") suitable for use in a variety of cutting and stapling procedures, such as a gastrointestinal anastomosis procedure. Linear surgical stapler (10) includes a cartridge half (12) (also referred to as a "reload half") and an anvil half (14) configured to releasably couple together to clamp tissue therebetween for simultaneous cutting and stapling of the clamped tissue.

Cartridge half (12) includes a first elongate member in the form of an elongate cartridge channel (16) having a proximal frame portion (18) and a distal jaw portion (20). Proximal frame portion (18) slidably retains a firing assembly (110) and includes a laterally opposed pair of upright side flanges (22). Each side flange (22) includes a vertical slot (24) arranged at a distal end thereof, and a tapered notch (26) arranged at a proximal end thereof. An outwardly projecting stiffening rib (28) extends longitudinally between the distal slot (24) and proximal notch (26) of each side flange (22) and is configured to provide the side flange (22) with enhanced stiffness. An outwardly flared upper segment (30) defines an upper edge of a proximal portion of each side flange (22) and is configured to facilitate receipt of anvil half (14) by cartridge half (12). Each side flange (22) further includes an elongate firing slot (32) extending longitudinally between proximal notch (26) and distal slot (24) along a lower side of side flange (22). Elongate firing slots (32) are configured to guide firing assembly (110) between proximal and distal positions. Firing assembly (110) is described in greater detail below in connection with FIG. 8.

Figure 4:
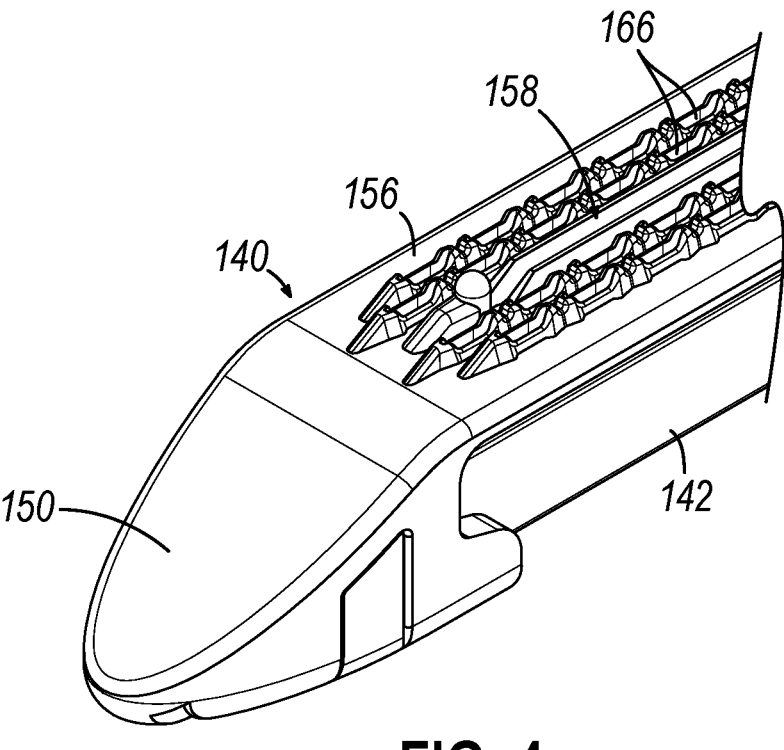
FIG. 4 depicts a perspective view of a distal end portion of the staple cartridge of FIG. 2.

Distal jaw portion (20) of cartridge channel (16) is configured to releasably receive a staple cartridge (140) (or "reload"). As shown in FIG. 4, staple cartridge (140) includes a cartridge body (142) having an upper side that defines a first stapling surface in the form of a deck (156) having a plurality of staple openings (166) that house a plurality of staples and corresponding staple drivers.

Cartridge half (12) further includes a clamp member in the form of a clamp lever (40) (also referred to as a "clamp arm" or "latch lever") pivotably coupled to cartridge channel (16) with a clamp lever pivot pin (42), which is arranged in approximate alignment with distal slots (24) of cartridge channel side flanges (22). Clamp lever (40) includes an elongate lever arm (44) having a free proximal end (46) and a distal end that is pivotably coupled to a lower portion of cartridge channel (16) with pivot pin (42). A pair of opposed jaws (48) extend distally from the distal end of lever arm (44) alongside cartridge channel side flanges (22). Each jaw (48) includes a curved slot (50) having a closed proximal end and an open distal end configured to receive a latch pin (68) of anvil half (14), as described below.

Figure 9A:
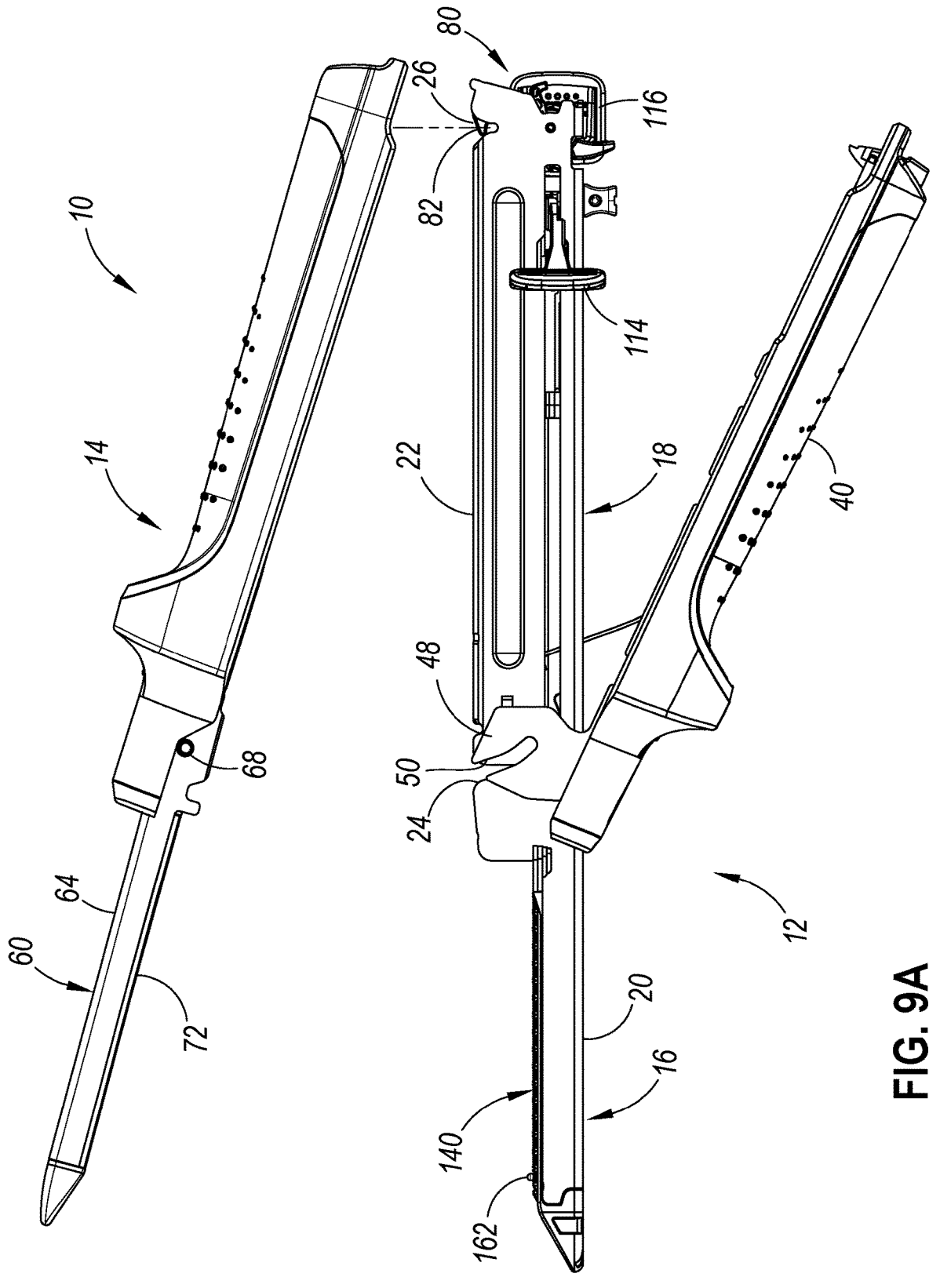
FIG. 9A depicts a side elevational view of the linear surgical stapler of FIG. 1, showing the stapler halves separated from one another with the clamp lever in the open position.
Figure 9B:
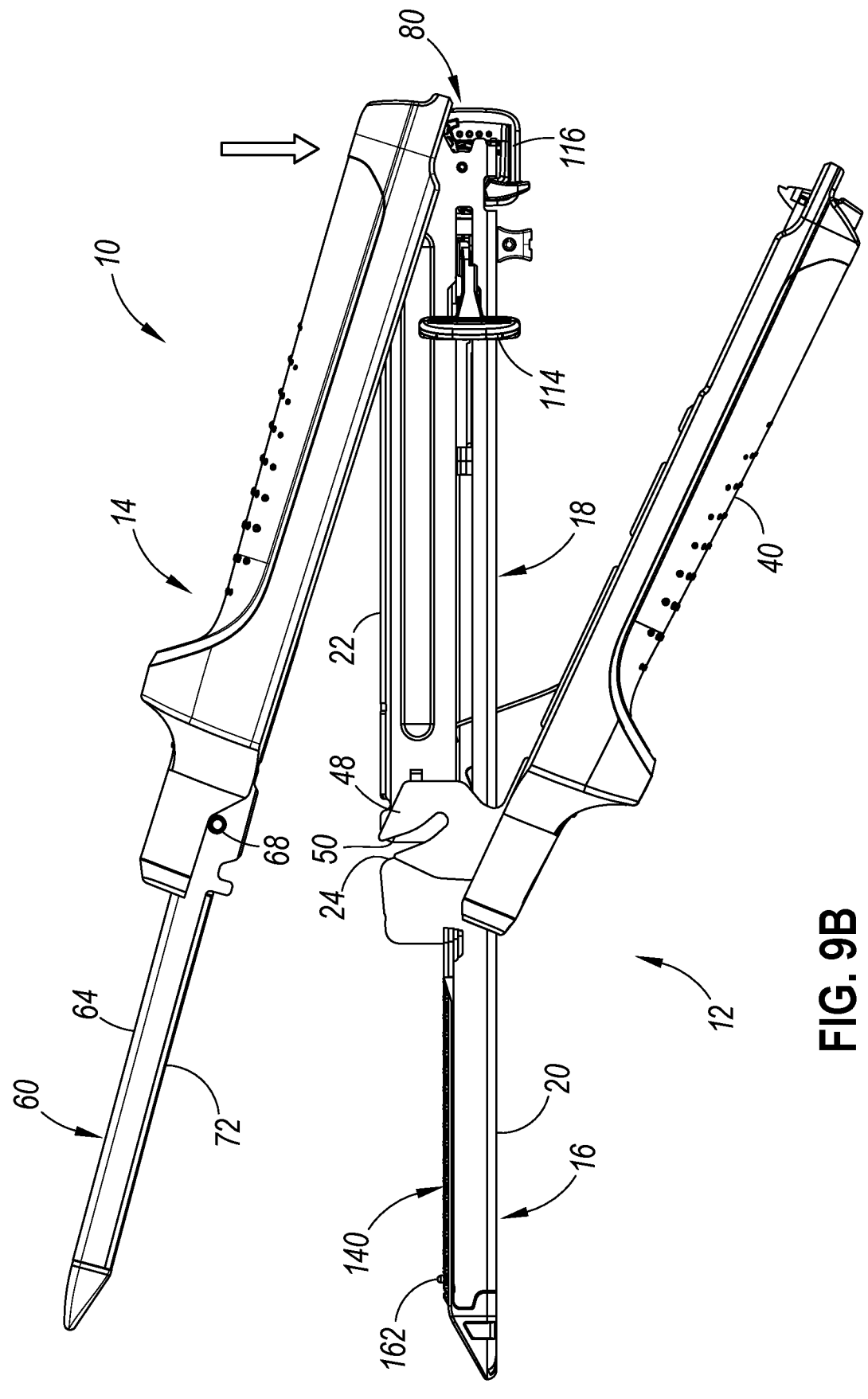
FIG. 9B depicts a side elevational view of the linear surgical stapler of FIG. 1, showing proximal ends of the stapler halves coupled together while the clamp lever is in the open position to provide the stapler in a "hang-open" state.
Figure 9C:
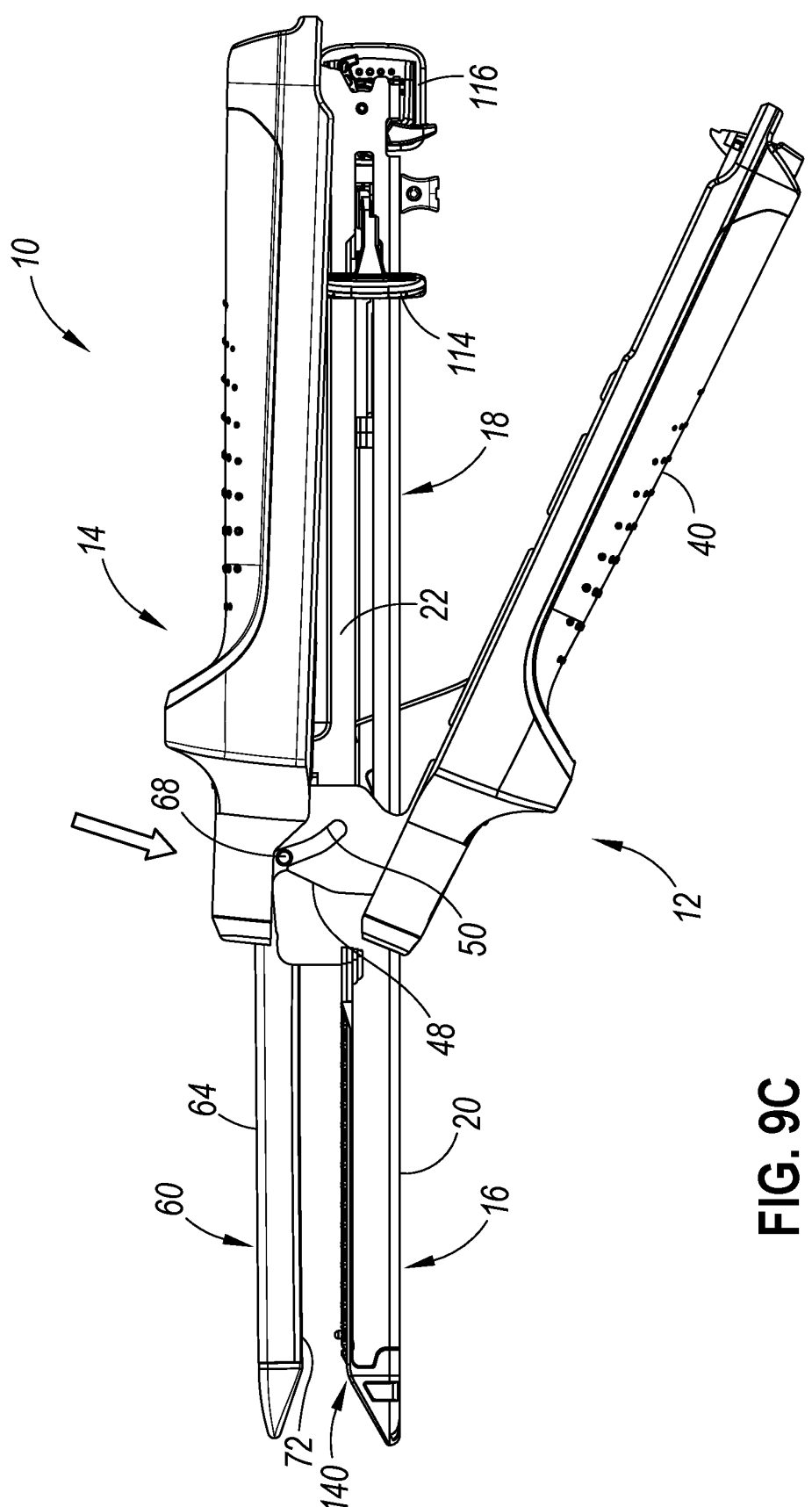
FIG. 9C depicts a side elevational view of the linear surgical stapler of FIG. 1, showing distal portions of the stapler halves having been approximated so that a distal pin of the anvil half is received by clamp lever jaws of the cartridge half.
Figure 9D:
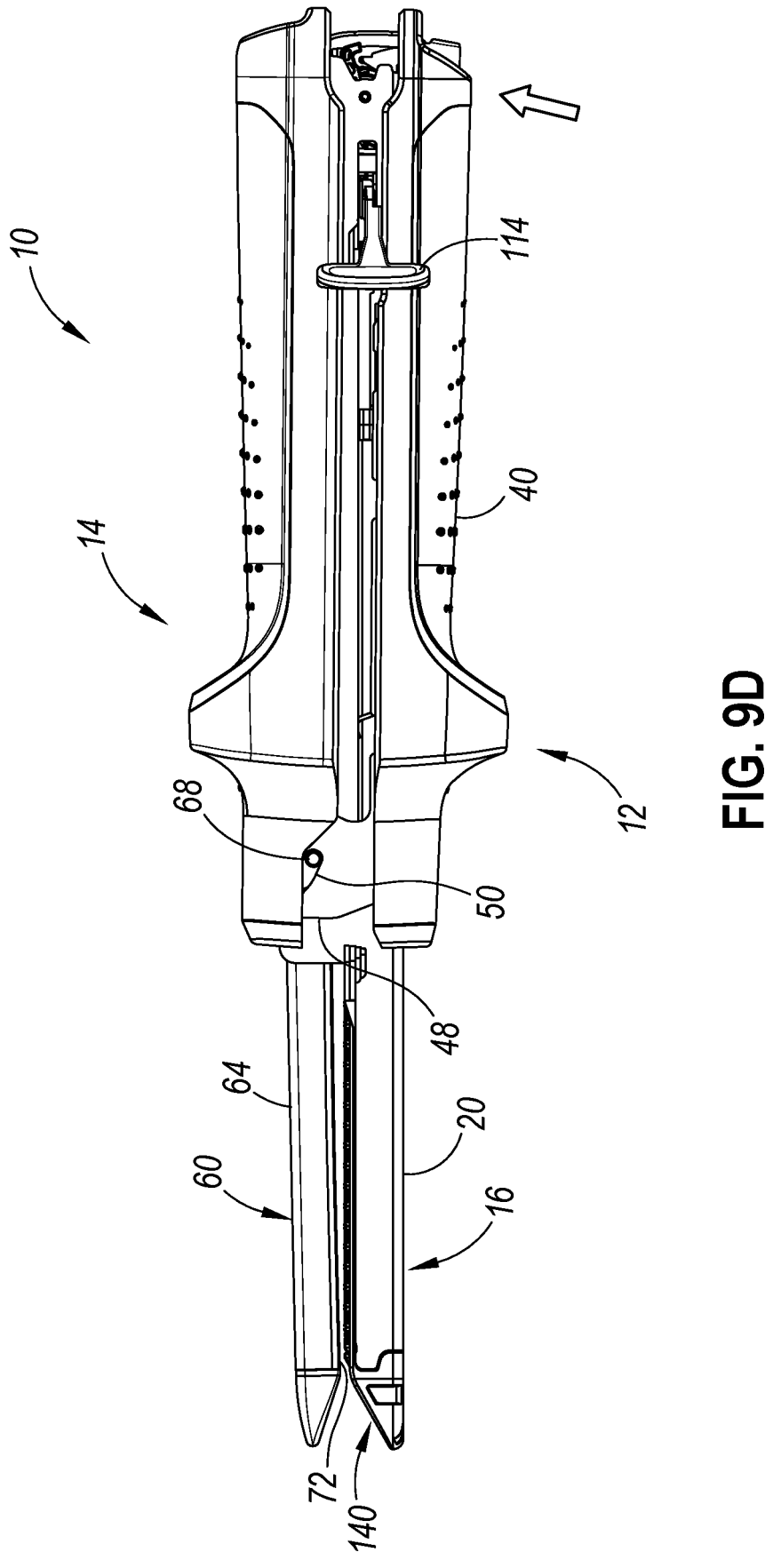
FIG. 9D depicts a side elevational view of the linear surgical stapler of FIG. 1, showing closure of the clamp lever to fully clamp the stapler halves together.

Clamp lever (40) is operable to pivot relative to cartridge channel (16) between an open position in which proximal end (46) of lever arm (44) is spaced from cartridge channel frame portion (18) as shown in FIGS. 9A-9C described below, and a closed position in which proximal end (46) confronts cartridge channel frame portion (18) as shown in FIG. 9D described below. Actuation of clamp lever (40) from the open position to the closed position operates to capture the opposed lateral ends of latch pin (68) within clamp lever jaw slots (50), and thereby clamp anvil half (14) against cartridge half (12), as shown and described below in connection with FIGS. 9C-9D. In that regard, the curvature of each jaw slot (50) defines respective upper and lower camming surfaces configured to engage and draw the respective lateral end of latch pin (68) toward cartridge channel (16) as clamp lever (40) is pivotably closed. A resilient member shown in the form of a leaf spring (52) biases lever arm (44) toward the open position. Accordingly, leaf spring (52) promotes disengagement of clamp lever jaws (48) from anvil half latch pin (68) upon initial advancement of clamp lever (40) from the closed position toward the open position.

As best shown in FIG. 2, clamp lever (40) further includes a latch member (54) arranged at proximal end (46) of lever arm (44). Clamp lever latch member (54) is configured to resiliently and releasably engage a proximal end of cartridge channel frame portion (18) and thereby releasably retain clamp lever (40) in the closed position, for instance while stapler (10) is being fired. Clamp lever latch member (54) may be further configured in accordance with the teachings of U.S. Pat. No. 11,278,285, entitled "Clamping Assembly for Linear Surgical Stapler," issued Mar. 22, 2022, the disclosure of which is incorporated by reference herein.

Anvil half (14) of linear surgical stapler (10) includes a second elongate member in the form of an elongate anvil channel (60) having a proximal frame portion (62) and a distal jaw portion (64). Proximal frame portion (62) includes a laterally opposed pair of upright side flanges (66) that are configured to be received between cartridge channel side flanges (22) when anvil half (14) is coupled with cartridge half (12). A distal latch projection in the form of latch pin (68) extends laterally through the distal ends of anvil channel side flanges (66), and a proximal pivot projection in the form of a proximal pin (70) extends laterally through the proximal ends of anvil channel side flanges (66). Anvil half pins (68, 70) are configured to facilitate coupling of anvil half (14) with cartridge half (12), as described below.

Figure 3:
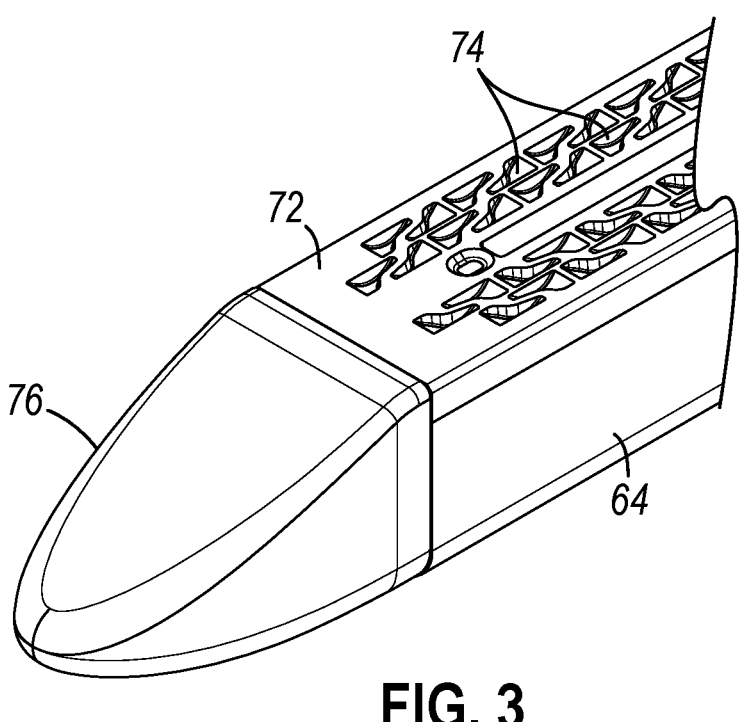
FIG. 3 depicts a perspective view of a distal end portion of the anvil half of the linear surgical stapler of FIG. 1.

As shown in FIGS. 2 and 3, distal jaw portion (64) of anvil half (14) supports an anvil plate (72) that defines a second stapling surface in the form of an anvil surface having a plurality of staple forming pockets (74) configured to deform legs of staples ejected by staple cartridge (140) when stapler (10) is fired. Staple forming pockets (74) of the present example may be formed via a coining process and are configured to form each staple of staple cartridge (140) with a three-dimensional shape in which the legs of each formed staple are laterally offset from one another so as to provide the formed staple with a non-planar shape, for example as disclosed in U.S. Pat. No. 11,229,433, entitled "Linear Surgical Stapler," issued Jan. 25, 2022, the disclosure of which is incorporated by reference herein. Anvil channel (60), anvil plate (72), and staple forming pockets (74) may be formed in one or more of the manners disclosed in U.S. Pat. Nos. 11,229,433; 11,045,193, entitled "Anvil Assembly for Linear Surgical Stapler," issued Jun. 29, 2021; and/or U.S. Pub. No. 2022/0142641, entitled "System and Method for Forming Pockets in Anvil of Surgical Stapler," published May 12, 2022, issued as U.S. Pat. No. 12,016,555 on Jun. 25, 2024, the disclosures of which are incorporated by reference herein. For instance, distal jaw portion (64) of anvil half (14) may be pre-formed with a curvature along its length that accommodates deflection of distal jaw portion (64) and anvil plate (72) when stapler halves (12, 14) are clamped together by clamp lever (40). Distal jaw portion (64) of anvil half (14) additionally supports a tapered distal tip member (76). In some versions, distal tip member (76) may be selectively extendable relative to distal jaw portion (64) in accordance with the teachings of U.S. Pat. No. 11,033,266, entitled "Decoupling Mechanism for Linear Surgical Stapler, issued Jun. 15, 2021, the disclosure of which is incorporated by reference herein.

As shown in FIG. 2, linear surgical stapler (10) further includes a pair of shrouds (56, 78) that cover select portions of stapler (10) and promote effective grip and manipulation of stapler (10) by an operator during use. In the present example, a clamp lever shroud (56) is affixed to and covers an outwardly facing side of clamp lever (40) such that clamp lever shroud (56) is configured to pivot with clamp lever (40) relative to cartridge channel (16). Additionally, an anvil shroud (78) is affixed to and covers an outwardly facing side of anvil channel (60). In some versions, anvil shroud (78) may be coupled with anvil channel (60) via interaction between pins (68, 70) and one or more tabs, ribs, or other structures that are disposed within an interior of anvil shroud (78) and include an opening, slot, keyhole, or other feature configured to receive a respective one of pins (68, 70). By way of example only, shrouds (56, 78) may be affixed using one or more of the teachings of U.S. Pat. No. 11,278,285, incorporated by reference above. In other versions, shrouds (56, 78) may be coupled with clamp lever (40) and anvil channel (60) in a variety of other suitable manners readily apparent to those of ordinary skill in the art in view of the teachings herein.

As shown best in FIGS. 2 and 5-7, a proximal end of cartridge half (12) includes a retaining assembly (80) configured to releasably retain portions of anvil half (14) and firing assembly (110). Retaining assembly (80) of the present example includes a first movable retaining member in the form of an anvil latch member (82) and a second movable retaining member in the form of a detent member (84). Anvil latch member (82) and detent member (84) are rotatably coupled with a proximal end of cartridge channel (16) via a laterally extending pin (85) arranged proximally of firing slots (32), and members (82, 84) are resiliently biased in opposite rotational directions by a resilient member in the form of a torsion spring (86) positioned between members (82, 84).

Anvil latch member (82) includes a central body (88), a latch finger (90) extending upwardly from central body (88), and a release button (92) extending downwardly from central body (88) though a base wall of proximal frame portion (18) of cartridge channel (16). An upper end of latch finger (90) tapers distally and is configured to releasably capture proximal anvil pin (70) of anvil half (14) with an angled latching surface (94) that overlies proximal anvil pin (70) once captured. Anvil latch member (82) further includes a pin ejection feature in the form of an angled projection (96) extending distally from a base portion of latch finger (90) and which defines an ejection cam ramp (98) that faces proximally toward latch finger (90).

Detent member (84) of proximal retaining assembly (80) includes a generally cylindrical central body (100), a distal finger (102) extending distally from central body (100), and a proximal hook (104) extending proximally from central body (100). Distal finger (102) is configured to releasably engage a proximal end of firing assembly (110) and thereby retain firing assembly (110) in a proximal home position. Proximal hook (104) is configured to overlie and capture an upper tip of clamp lever latch member (54) when clamp lever (40) is fully closed and firing assembly (110) is translated distally from its proximal home position, thereby preventing clamp lever (40) from opening during a firing stroke, for example as described in greater detail in U.S. Pat. No. 11,278,285, incorporated by reference above.

In use, with stapler halves (12, 14) coupled together at their proximal ends such that proximal anvil pin (70) is retained by anvil latch member (82), and with clamp lever (40) in the open position, distal actuation of lower release button (92) causes anvil latch member (82) to rotate about pin (85) such that ejection cam ramp (98) advances proximally to drive proximal anvil pin (70) upwardly out of proximal tapered notches (26) of cartridge channel (16). Cartridge half (12) of the present version further includes a stationary finger grip projection (106) that extends downwardly from a base wall of proximal frame portion (18) of cartridge channel (16) at a location distal to lower release button (92), and is configured to facilitate actuation of release button (92). In particular, a user may apply his or her thumb to a proximal side of release button (92) and one or more fingers to a distal side of finger grip projection (106), and then squeeze release button (92) distally toward stationary finger grip projection (106) to rotate latch finger (90) out of engagement with proximal anvil pin (70) and eject pin (70) upwardly from cartridge channel (16) with ejection cam ramp (98).

Retaining assembly (80) and related components of cartridge half (12) may be further configured and operable in accordance with one or more teachings of U.S. Pat. No. 10,898,187, entitled "Firing System for Linear Surgical Stapler," issued Jan. 26, 2021, the disclosure of which is incorporated by reference herein; and/or U.S. Pat. No. 11,033,266, incorporated by reference above.

Figure 8:
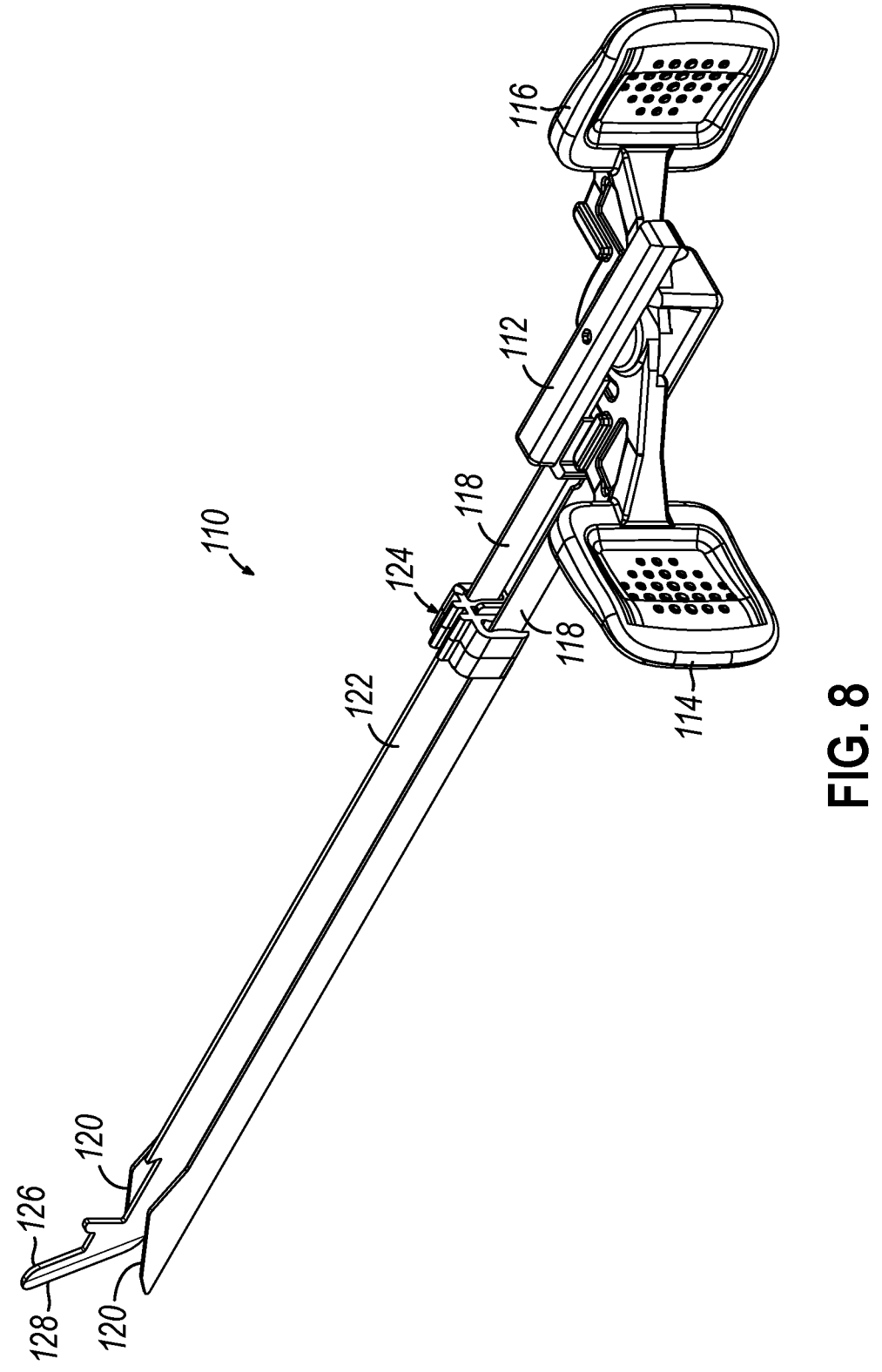
FIG. 8 depicts a perspective view of the firing assembly of FIG. 5.

As shown in FIG. 8, firing assembly (110) of cartridge half (12) includes a slide block (112), a pair of actuators (114, 116) (or "firing knobs") pivotably coupled to slide block (112), and a set of elongate beams (118, 122) extending distally from slide block (112). A pair of side beams (118) are coupled at their proximal ends to a distal end of slide block (112) and terminate distally in a pair of cam ramps (120). Cam ramps (120) are configured to engage the undersides of staple drivers (not shown) housed within staple cartridge (140) and actuate staple drivers (not shown) upwardly to thereby drive (or "fire") staples from cartridge (140) into tissue clamped between staple cartridge (140) and anvil plate (72). A center beam (122) is coupled with side beams (118) via a bridge member (124) (or "knife block") spaced distally from slide block (112). Center beam (122) terminates distally in a distally angled knife member (126) having a distal cutting edge (128) configured to cut tissue clamped between the distal portions of stapler halves (12, 14).

Each actuator (114, 116) of firing assembly (110) is configured and rotatable relative to slide block (112) between a deployed position and a retracted position such that only one actuator (114, 116) may be deployed at a time, for example as disclosed in U.S. Pat. No. 10,898,187, incorporated by reference above. In the deployed position, an actuator (114, 116) may be driven distally by an operator to actuate firing assembly (110) distally through stapler (10) and thereby simultaneously cut and staple tissue clamped between stapler halves (12, 14).

B. Illustrative Use of Linear Surgical Stapler

Figure 5:
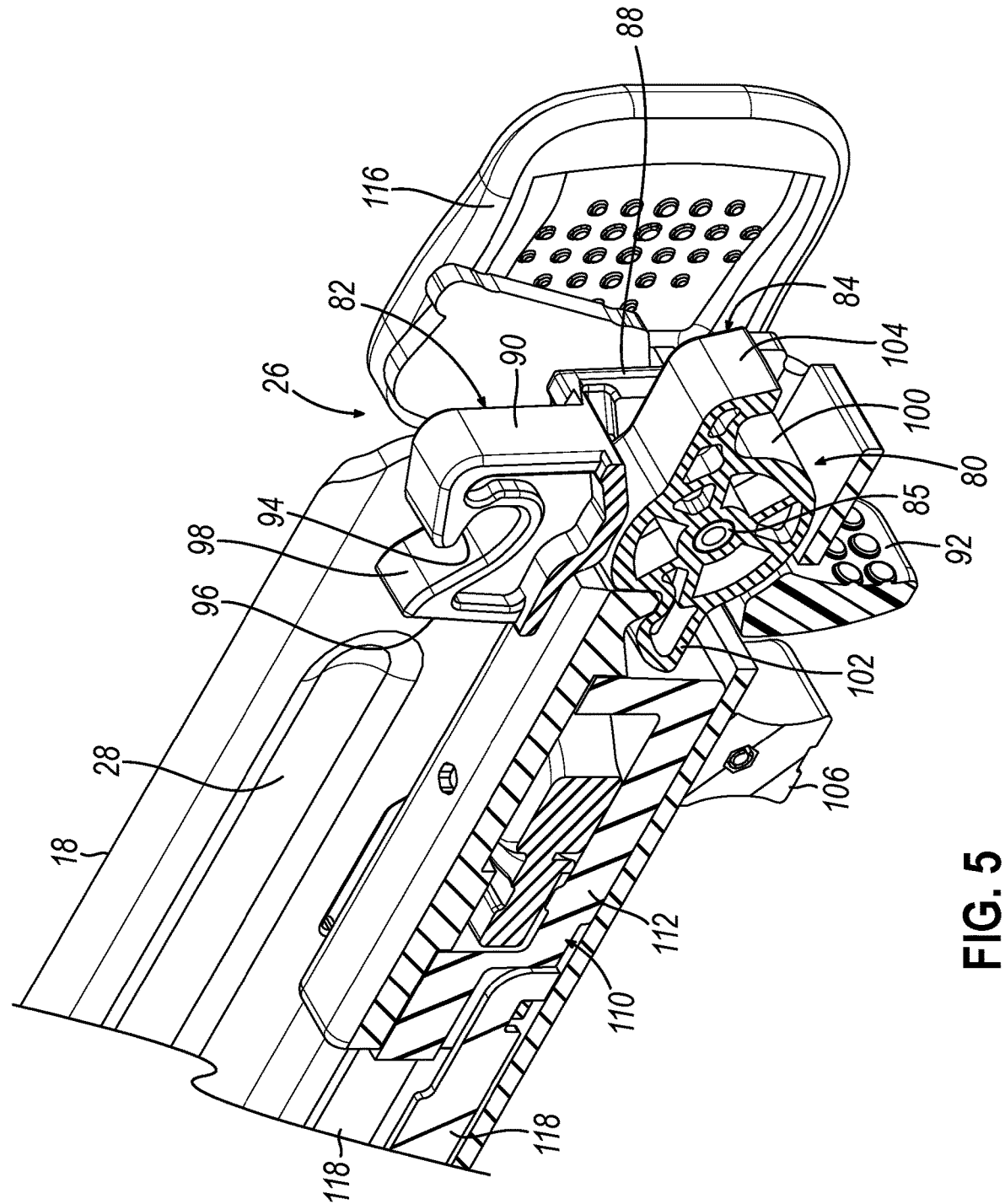
FIG. 5 depicts a cross-sectional perspective view of a proximal portion of the cartridge half of the linear surgical stapler of FIG. 1 with the clamp lever in an open position to reveal details of a firing assembly and a retaining assembly of the cartridge half.

FIGS. 9A-9E show illustrative coupling of stapler halves (12, 14) and subsequent firing of assembled stapler (10) during a surgical procedure. As shown in FIG. 9A, clamp lever (40) of cartridge half (12) is provided in the open position so that jaw slots (50) align with vertical slots (24) of cartridge channel side flanges (22). Additionally, firing assembly (110) is maintained in its proximal home position by detent member (84) of retaining assembly (80), as shown in FIG. 5 described above. At this stage, a section of tissue (not shown) to be stapled and cut may be positioned over the top of staple cartridge (140) disposed in distal jaw portion (20) of cartridge half (12). Alternatively, the tissue may be positioned over staple cartridge (140) following coupling of the proximal ends of stapler halves (12, 14), described below.

As shown in FIGS. 9A-9B, the proximal ends of stapler halves (12, 14) are aligned with one another, and proximal anvil pin (70) is directed downwardly into proximal tapered notches (26) of cartridge channel (16) to engage latch finger (90) of anvil latch member (82). This engagement forces anvil latch member (82) to resiliently rotate clockwise, thus enabling latch finger (90) to capture anvil pin (70) and thereby releasably couple together the proximal ends of stapler halves (12, 14), as seen in FIG. 9B. With clamp lever (40) still in the open position as shown in FIG. 9B, stapler (10) is provided in a "hang-open" state such that stapler (10) may be held single-handedly by anvil half (14) while cartridge half (12) remains coupled to anvil half (14). As shown in FIG. 9C, and with clamp lever (40) remaining in the open position, anvil half (14) is rotated toward anvil half (14) about proximal anvil pin (70) so that distal latch pin (68) of anvil half (14) is received into vertical slots (24) of cartridge channel side flanges (22) and jaw slots (50) of clamp lever (40). Distal jaw portions (20, 64) of stapler halves (12, 14) are now in a partially approximated state such that tissue received therebetween may be finally adjusted before clamping.

As shown in FIG. 9D, clamp lever (40) is closed to draw anvil latch pin (68) against the closed proximal ends of jaw slots (50) and thereby fully clamp anvil half (14) against cartridge half (12), with tissue (not shown) clamped between the stapling surfaces defined by staple cartridge (140) and anvil plate (72). A slight transverse gap is defined between staple cartridge (140) and anvil plate (72) by a tissue gap post (162) of staple cartridge (140), thus accommodating the tissue therebetween with a predetermined degree of tissue compression. As shown in FIGS. 9A and 9B, tissue gap post (162) is disposed at a distal end of staple cartridge (140) and is configured to contact a distal end of anvil plate (72) when stapler (10) is in the fully clamped state shown in FIG. 19D. In response to clamp lever (40) reaching the fully closed position, clamp lever latch member (54) may rotate to capture a proximal end of a base wall of cartridge channel (16) and thereby assume a latched state in which clamp lever latch member (54) maintains clamp lever (40) in the closed position.

Figure 9E:
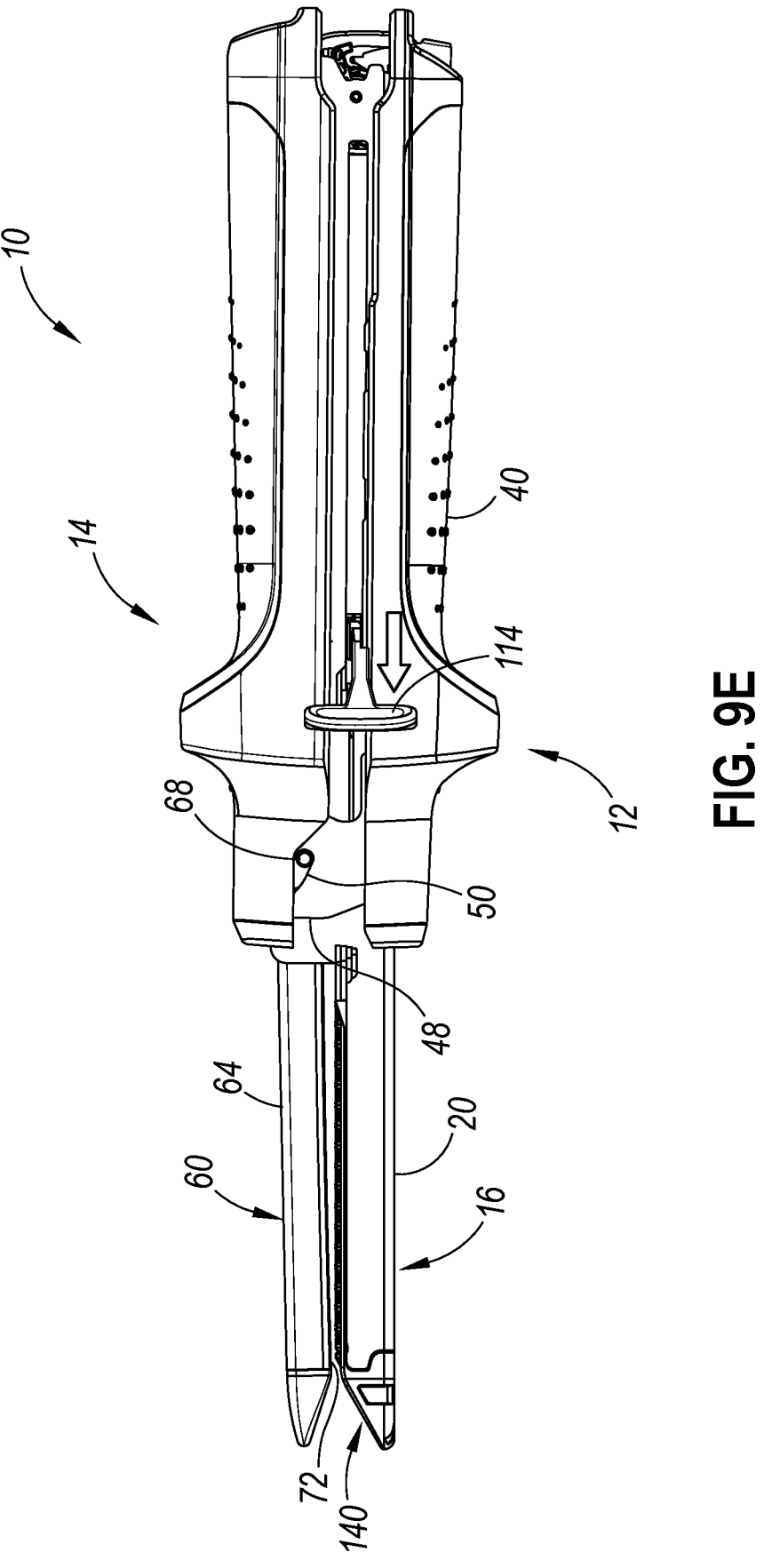
FIG. 9E depicts a side elevational view of the linear surgical stapler of FIG. 1, showing distal actuation of the firing assembly while the stapler halves are in the fully clamped state.

As shown in FIG. 9E, upon reaching the fully clamped state, stapler (10) may be fired by driving a deployed actuator (114, 116) of firing assembly (110) distally along proximal frame portion (18) of cartridge half (12). This action causes elongate beams (118, 122) of firing assembly (110) to translate distally through corresponding channels formed in staple cartridge (140) and thereby fire staples into the clamped tissue via cam ramps (120) and staple drivers (not shown), and simultaneously cut the clamped tissue with knife member (126). Following completion of the firing stroke, firing assembly (110) is returned to its proximal home position via the actuator (114, 116). Clamp lever latch member (54) may then be depressed to release the proximal end of clamp lever (40) from cartridge channel (16), thus permitting clamp lever (40) to be re-opened. Then, release button (92) of retaining assembly (80) may be depressed to release anvil half (14) from cartridge half (12) so that stapler halves (12, 14) may be separated from one another, thereby releasing the newly stapled and severed tissue. It will be understood that in some versions, stapler (10) may include additional features to promote decoupling of stapler halves (12, 14), for example as disclosed in U.S. Pat. No. 11,033, 266, incorporated by reference above.

D. Linear Surgical Stapler Having Lockout Mechanism

As mentioned above, anvil latch pin (68) of anvil half (14) is received within curved slots (50) of jaws (48) such that clamp lever (40) may pivot from the open position (see FIG. 9C) toward the closed position (see FIG. 9D) to thereby clamp anvil half (14) toward cartridge half (12) to thereby grasp and clamp tissue. Further, grasped tissue located between the stapling surfaces of staple cartridge (140) and anvil plate (72) may be severed and stapled.

Figure 10A:
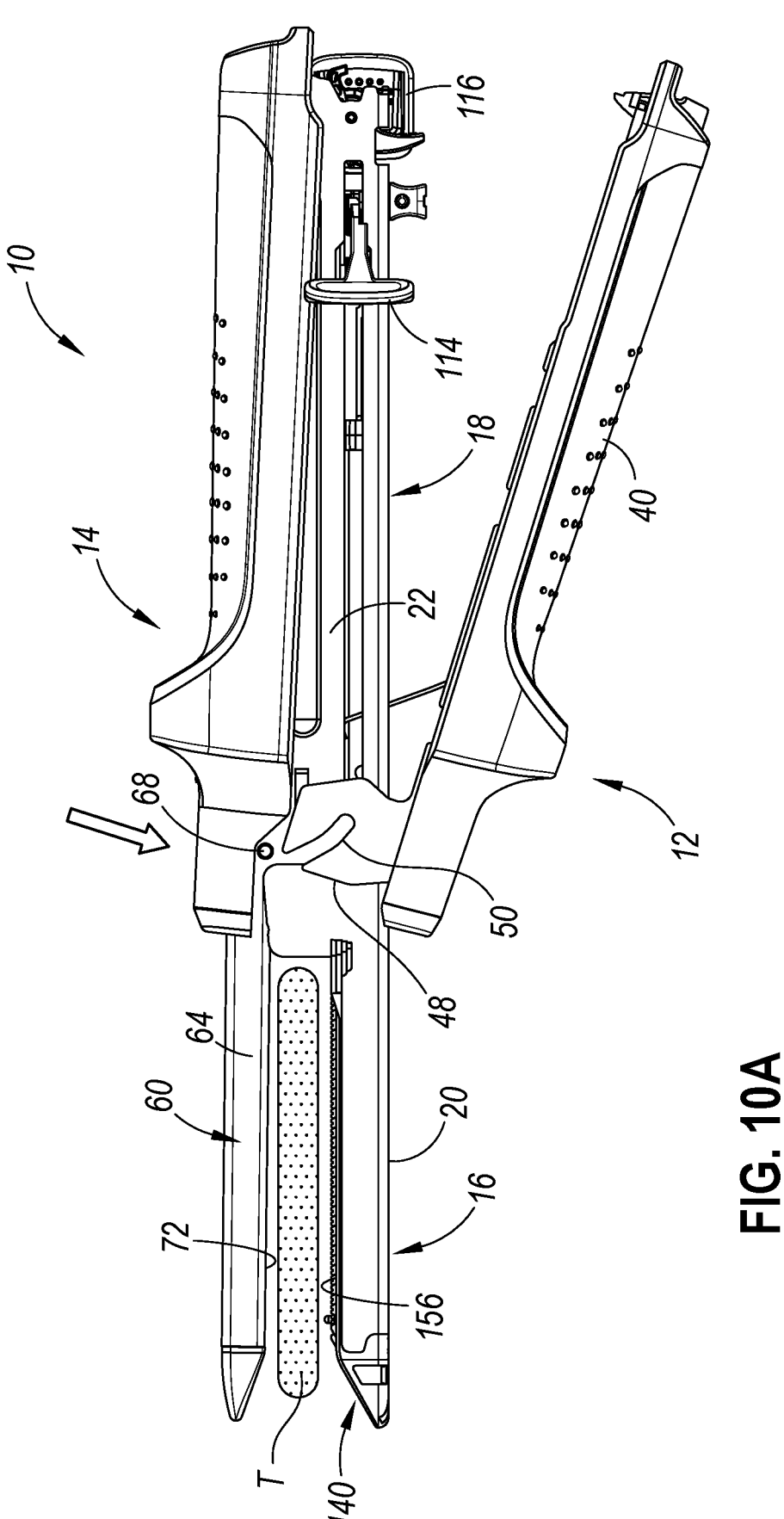
FIG. 10A depicts a side elevational view of the linear surgical stapler of FIG. 1, showing distal portions of the stapler halves having been approximated with tissue therebetween while the distal pin of FIG. 9C is misaligned with clamp lever jaws of the cartridge half.
Figure 10B:
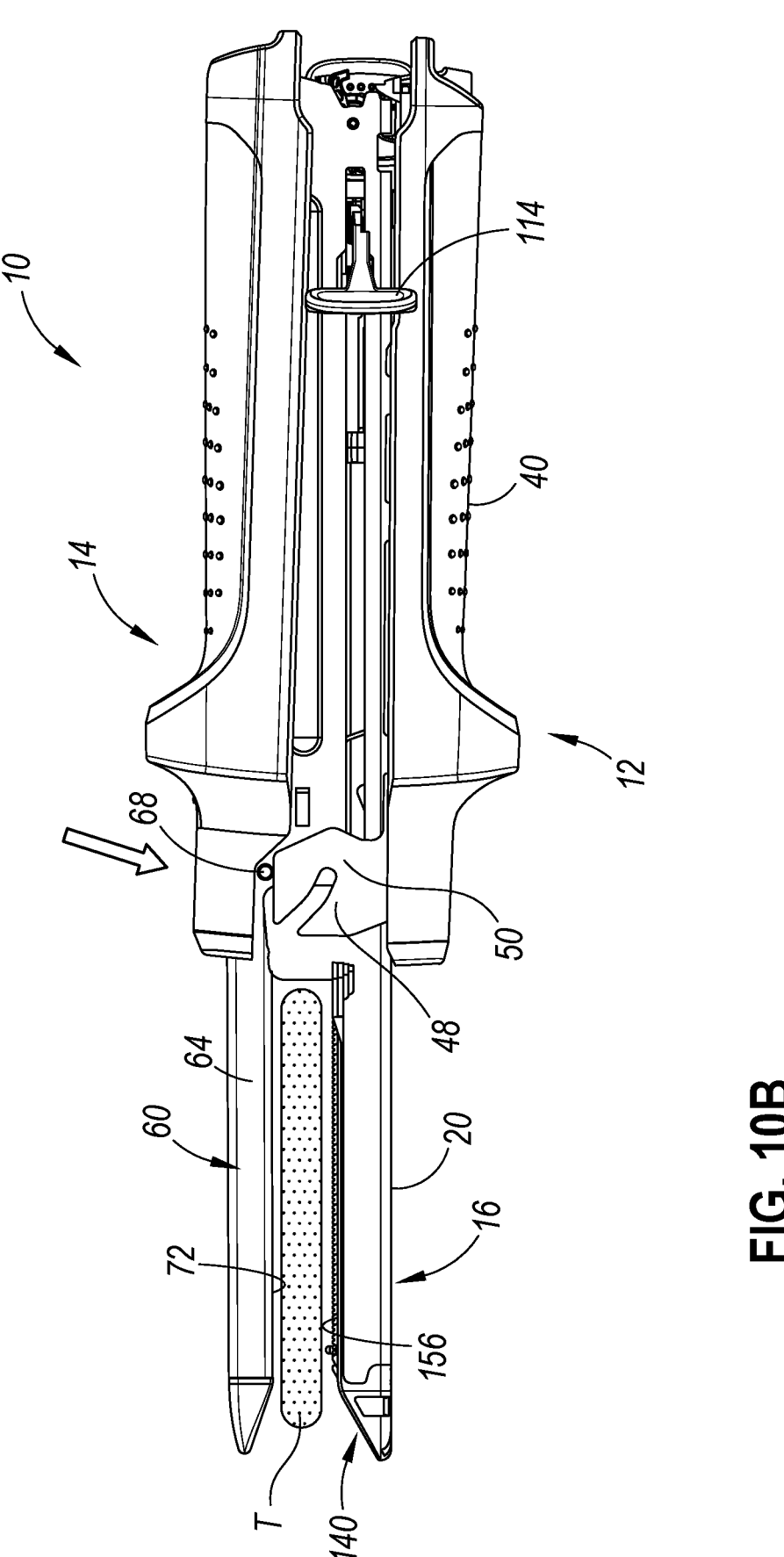
FIG. 10B depicts a side elevational view of the linear surgical stapler of FIG. 1, showing closure of the clamp lever while the distal pin of FIG. 9C is still misaligned with clamp lever jaws of the cartridge half.

As shown between FIGS. 10A-10B, in instances where clamp lever (40) is pivoted from the open position toward the closed position without anvil latch pin (68) received within curved slots (50) of jaws (48), tissue located between staple cartridge (140) and anvil plate (72) may never be properly clamped or grasped, leaving an undesirably large gap distance (d2). If gap distance (d2) is too large, staples fired from staple cartridge toward anvil plate (72) may not suitably form, either creating malformed staples or "open" staples, either of which may fail to suitably engage staple forming pockets (74) of anvil plate (72). Therefore, it may be desirable to prevent actuation of firing assembly (110) unless tissue is suitably clamped with clamp lever (40) in the closed positioned while anvil latch pin (68) is suitably housed within curved slots (50), as illustrated in FIG. 9D.

Figure 11:
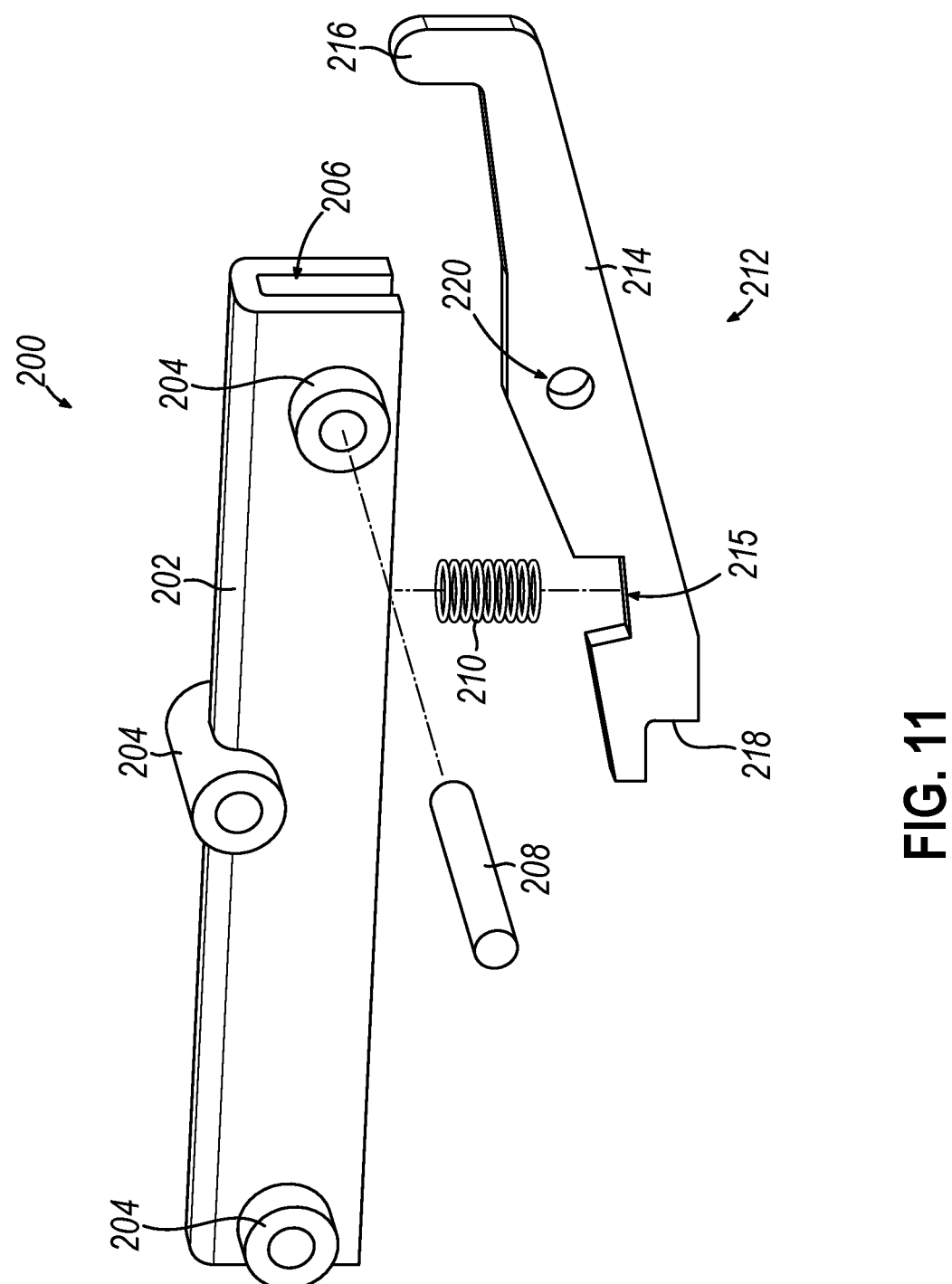
FIG. 11 depicts an exploded perspective view of a lockout assembly that may be readily incorporated into the linear surgical stapler of FIG. 1.
Figure 12:
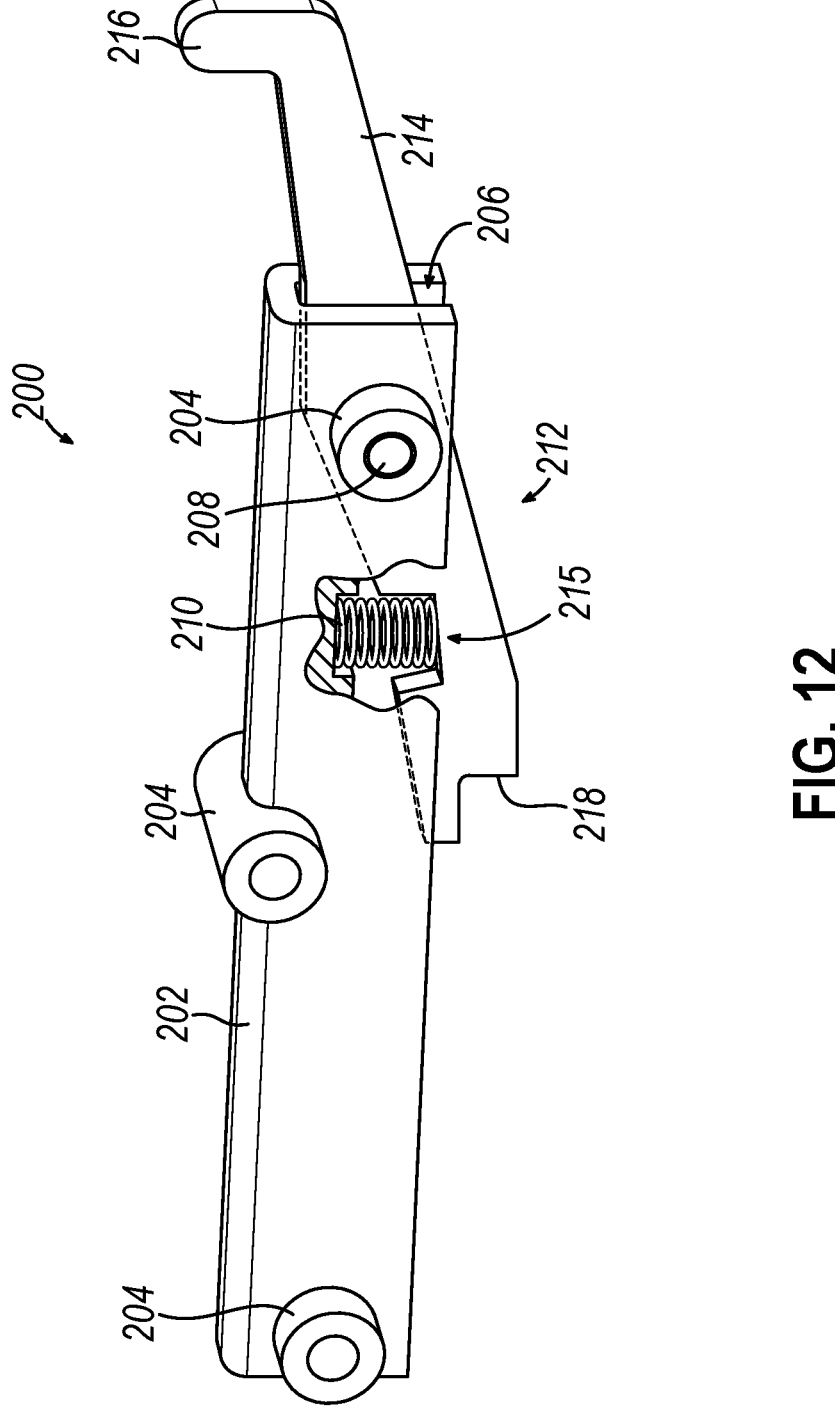
FIG. 12 depicts a perspective view of the lockout assembly of FIG. 11, with sections omitted for purposes of clarity.
Figure 13A:
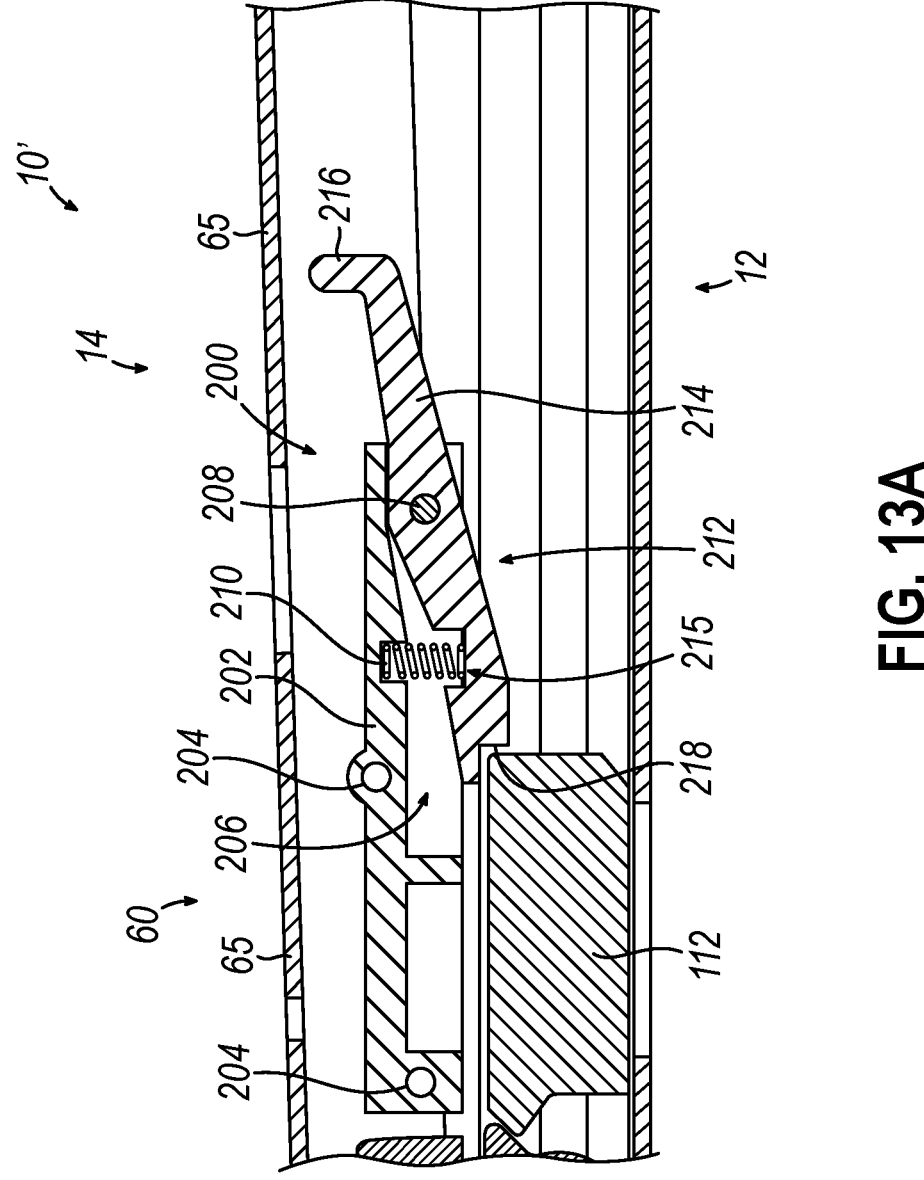
FIG. 13A depicts a cross-sectional view of the lockout assembly of FIG. 11 incorporated into the linear surgical stapler of FIG. 1, where the lockout assembly is in a locked configuration and the firing assembly of FIG. 5 is in a proximal, unfired position.
Figure 13B:
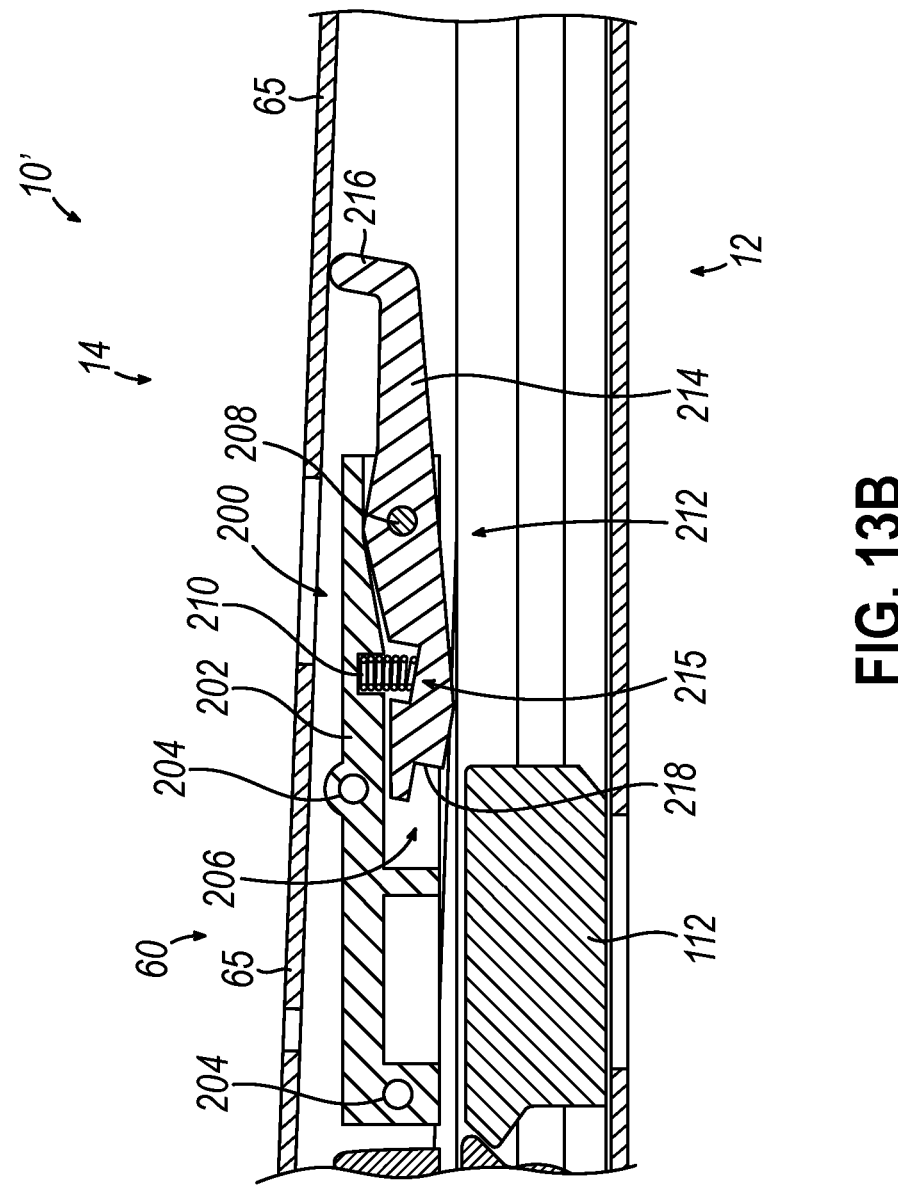
FIG. 13B depicts a cross-sectional view of the lockout assembly of FIG. 11 incorporated into the linear surgical stapler of FIG. 1, where the lockout assembly is in an unlocked configuration and the firing assembly of FIG. 5 is in a proximal, unfired position.
Figure 13C:
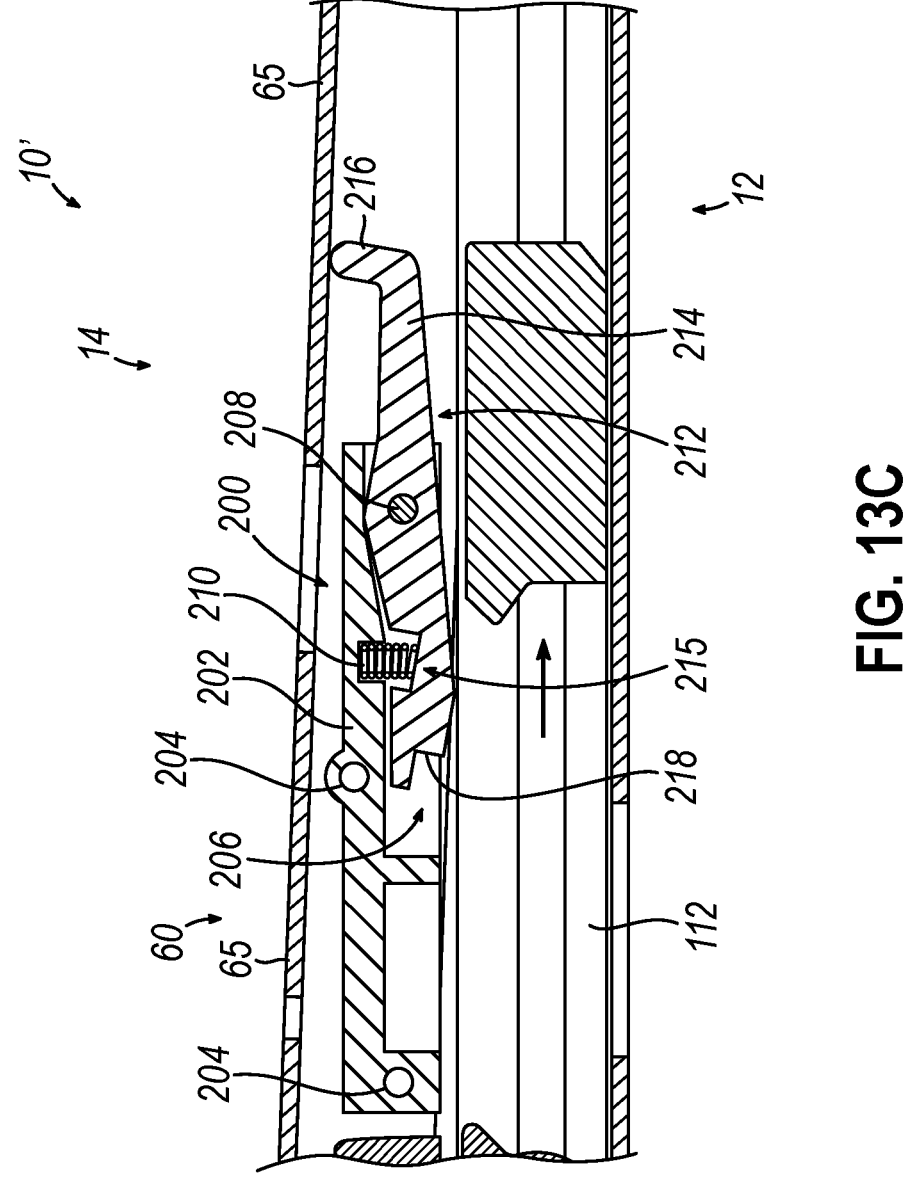
FIG. 13C depicts a cross-sectional view of the lockout assembly of FIG. 11 incorporated into the linear surgical stapler of FIG. 1, where the lockout assembly is in the unlocked configuration and the firing assembly of FIG. 5 is actuated distally toward a fired position.

FIGS. 11-12 show an illustrative lockout mechanism (200) that may be readily incorporated into linear stapler (10) in order to form a modified linear stapler (10') shown in FIGS. 13A-13C. As will be described in greater detail below, lockout mechanism (200) is configured to inhibit distal actuation of firing assembly (110) until distal jaw portion (64) of anvil half (14) is in a suitable clamped position relative to cartridge half (12) indicative of clamp lever (40) being both in the closed position and suitably engaged with latch pin (68) via curved slots (50) of jaws (48) (see FIG. 9D). Therefore, if anvil half (14) is in an open position (see FIG. 9C), lockout mechanism (200) will inhibit distal actuation of firing assembly (110). Further, if anvil half (14) is pivoted toward cartridge half (12) into a position where a user believes anvil half (14) is clamped, but latch pin (68) is not suitably housed within curved slots (500) of jaws (48) (see FIG. 10B), lockout mechanism (200) will still inhibit distal actuation of firing assembly (110).

Lockout mechanism (200) includes a housing (202), a bias spring (210), and a lockout body (212). Housing (202) includes a plurality of coupling bosses (204). Coupling bosses (204) are configured to attach housing (202) to suitable portions of proximal frame portion (18) of cartridge half (12). For example, coupling bosses (204) may be configured to attach housing (202) to upright side flanges (22) of proximal frame portion (18). Therefore, housing (202) acts as a mechanical ground for lockout mechanism (200) to cartridge half (12). While coupling bosses (204) are used in the current example, housing (202) may be fixedly attached to proximal frame portion (18) via any suitable means as would be apparent to one skilled in the art in view of the teachings herein. Alternatively, housing (202) may be an integral component of proximal frame portion (18).

As shown in FIGS. 13A-13C, housing (202) is attached to suitable portions of proximal frame portion (18) such that lockout body (212) is adjacent to slide block (112) of firing assembly (110) in a pre-fired position. Housing (202) defines an elongate slot (206) that pivotally receives a portion of lockout body (212). Lockout body (212) is pivotally attached to housing (202) via a pivot pin (208) extending though a respective coupling boss (204) of housing (202) and a pivot hole (220) defined by lockout body (212).

As will be described in greater detail below, lockout body (212) is configured to pivot relative to housing (202) about pivot pin (208) between a locked configuration (see FIG. 13A) and an unlocked configuration (see FIGS. 13B-13C) in response to anvil half (14) reaching the suitable clamped position associated with latching pin (68) being contained within curved slots (50) of jaws (48) while clamp lever (40) is in the closed position. Further, lockout body (212) is configured to remain in the locked configuration if anvil half (14) is remains in the open position (similar to FIG. 9C), or if anvil half (14) is pivoted toward cartridge half (12) without latching pin (68) suitably contained within curved slots (50) of jaws (48) (similar to FIG. 10B).

Spring (210) is housed within elongate slot (206) of housing (202). Spring (210) is interposed between a portion of lockout body (212) and housing (202) in order to bias lockout body (212) relative to housing (202) into the locked configuration (see FIG. 13A). Spring (210) is configured to compress in response to lockout body (212) engaging with a top surface (65) of elongate anvil channel (60); thereby pivoting lockout body (212) from the locked configuration into the unlocked configuration (see FIGS. 13B-13C).

Lockout body (212) includes an elongate pivot arm (214) extending between an anvil engagement protrusion (216) and a slide block engagement face (218). Elongate pivot arm (214) defines pivot hole (220). Elongate pivot arm (214) also defines a spring notch (215) dimensioned to receive spring (210). Spring notch (215) is interposed between pivot hole (220) and slide block engagement face (218) such that spring (210) engages a portion of elongated arm (214) located between pivot hole (220) and slide block engagement face (218). In particular, spring (210) biases the portion of elongate pivot arm (214) proximal to pivot hole (220) away from housing (202); and also biases the portion of the elongate pivot arm (214) distal to pivot hole (220) toward anvil half (12).

Slide block engagement face (218) is configured to abut against or otherwise inhibit distal actuation of slide block (112) while lockout body (212) is in the locked configuration. Therefore, slide block engagement protrusion (218) is configured to abut against or otherwise inhibit distal action of slide block (112) while lockout body (212) is in the locked configuration. In the unlocked configuration, slide block engagement face (218) is removed from the firing path of slide block (112), therefore allowing slide bock (112) to actuate distally in accordance with the description herein.

Anvil engagement protrusion (216) is configured to contact a portion of anvil channel (60) in response to anvil half (14) reaching a suitable clamped position associated with latching pin (68) being contained within curved slots (50) of jaws (48) while clamp lever (40) is in the closed position. For example, anvil engagement protrusion (216) may be configured to contact top surface (65) of elongate anvil channel (60). As will be described in great detail below, engagement between anvil engagement protrusion (216) and anvil half (14) drives lockout body (212) from the locked configuration into the unlocked configuration, to thereby allow distal actuation of firing assembly (110) in accordance with the description herein.

FIGS. 13A-13C show an illustrative use of linear surgical stapler (10') and lockout assembly (200). At the moment shown in FIG. 13A, anvil half (14) is not suitably clamped via engagement with clamp lever (40) and latching pin (68) such that lockout mechanism (200) is in the locked configuration. In such instances, anvil half (14) may be in an open position (similar to FIG. 9C); or anvil half (14) may be in a position that a user believes to be clamped, but latch pin (68) is not suitably housed within curved slots (50) of jaws (48) (similar to FIG. 10B).

As mentioned above, spring (210) biases lockout body (212) into the locked configuration. While in the locked configuration, slide block engagement face (218) is directly adjacent to a distally facing surface of sliding block (112), therefore blocking distal actuation of sliding block (112). Therefore, if a user attempted to actuate firing assembly (110) in accordance with the description herein, engagement between sliding block (112) and slide block engagement face (218) will inhibit a user from doing so, indicating that anvil half (14) is not suitably clamped in accordance with the description herein.

FIG. 13B, shows anvil half (14) in a suitably clamped position relative to cartridge half (12) such that latch pin (68) is suitably housed within curved slots (50) of jaws (48) while clamp lever (40) is in the closed position. With anvil half (14) in the suitably clamped position, top surface (65) of elongate anvil channel (60) drives anvil engagement protrusion (216) downward, thereby pivoting lockout body (212) into the unlocked configuration and compressing spring (210). In the unlocked configuration, slide block engagement face (218) is pivoted out of the firing path of sliding block (112). In the current example, slide block engagement face (218) is pivoted into the confines of elongate slot (206).

As shown in FIG. 13C, with slide block engagement face (218) pivoted out of the firing path of sliding block (112), a user can actuate firing assembly (110) distally in accordance with the description herein to staple and sever tissue in accordance with description herein. Once firing assembly (110) is retracted to the pre-fired position (similar to the position shown in FIG. 13B), a user may then pivot clamp lever (40) to the open position to release tissue. Once anvil half (14) is unlatched form cartridge half (12) by pivoting clamp lever (40) from the closed position (similar to FIG. 9D) to the open position (similar to FIG. 9C), top surface (65) of elongate anvil channel (60) disengages anvil engagement protrusion (216) such that spring (210) pivots lockout body (212) back into the locked configuration as shown in FIG. 13A.

Figure 14:
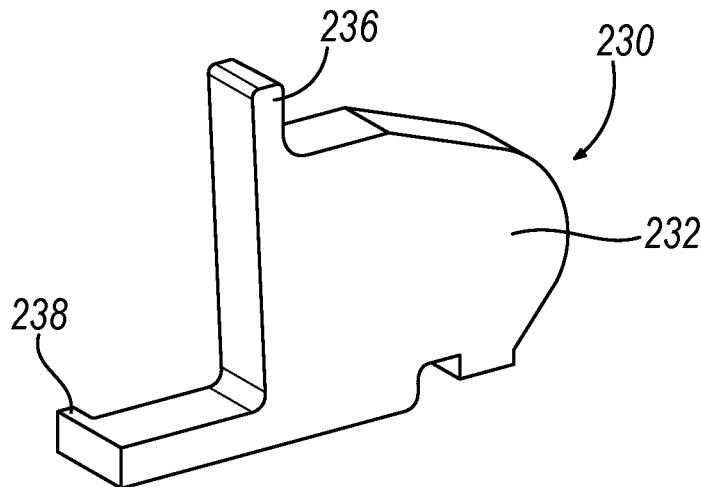
FIG. 14 depicts a perspective of an alternative lockout body that may be readily incorporated into the linear surgical stapler of FIG. 1.
Figure 15A:
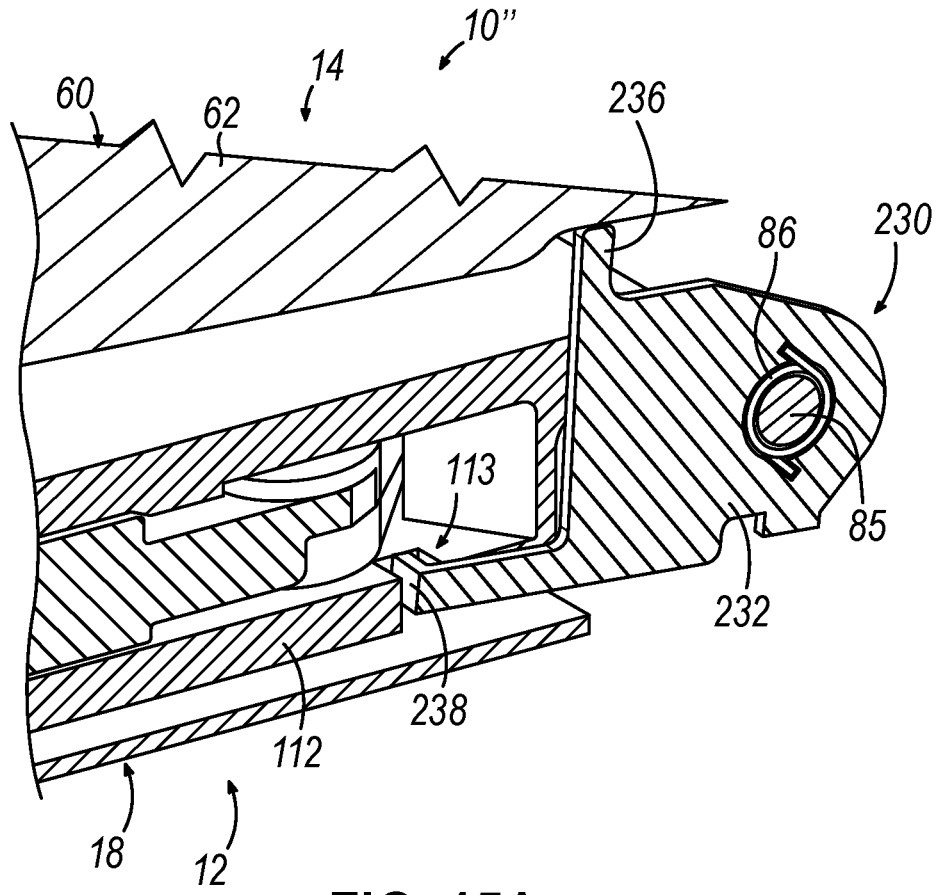
FIG. 15A depicts a sectional view of a lockout assembly including the lockout body of FIG. 14 incorporated into the linear surgical stapler of FIG. 1, where the lockout assembly is in a locked configuration and the firing assembly of FIG. 5 is in a proximal, unfired position.
Figures 15B, 15C:
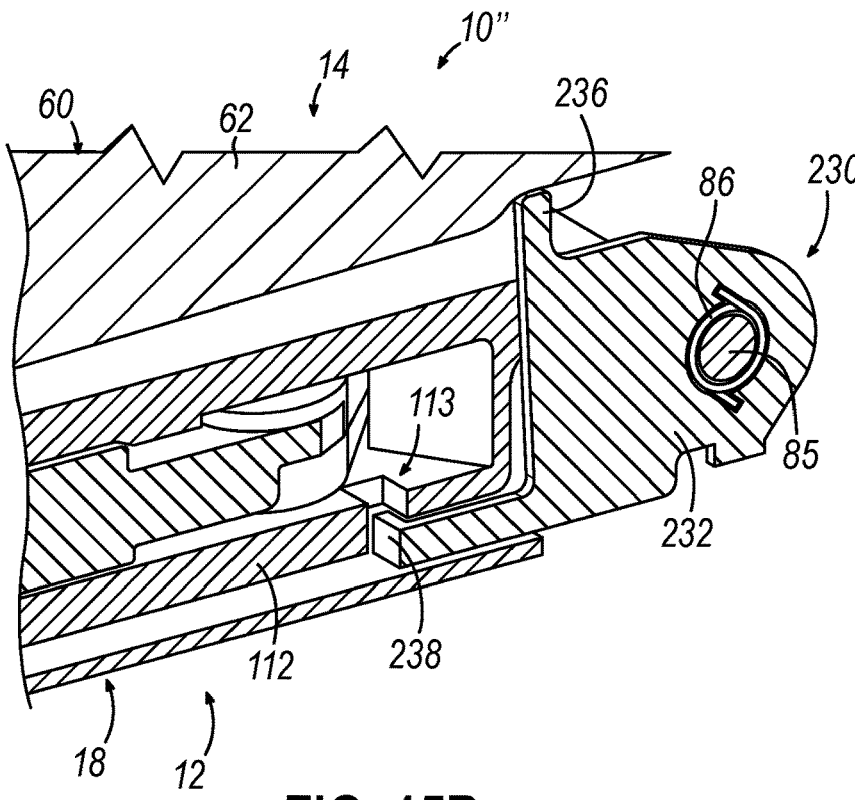
FIG. 15B depicts a sectional view of the lockout assembly of FIG. 15A incorporated into the linear surgical stapler of FIG. 1, where the lockout assembly is in an unlocked configuration and the firing assembly of FIG. 5 is in the proximal, unfired position.
FIG. 15C depicts a sectional view of the lockout assembly of FIG. 15A incorporated into the linear surgical stapler of FIG. 1, where the lockout assembly is in the unlocked configuration and the firing assembly of FIG. 5 is actuated distally toward a fired position.

FIG. 14 shows another illustrative lockout mechanism (230) that may be readily incorporated into linear stapler (10) in order to form a modified linear stapler (10") shown in FIGS. 15A-15C. Lockout mechanism (230) is configured to function in substantially similar to lockout mechanism (200) described above, with differences elaborated herein. Therefore, lockout mechanism (230) is configured to inhibit distal actuation of firing assembly (110) until distal jaw portion (64) of anvil half (14) is in a suitable clamped position relative to cartridge half (12) indicative of clamp lever (40) being both in the closed position and suitably engaged with latch pin (68) via curved slots (50) of jaws (48) (see FIG. 9D).

Lockout mechanism (230) includes a pivoting lockout body (232) having an anvil engagement protrusion (236) and a slide block engagement protrusion (238). Lockout body (232) is pivotally attached to laterally extending pin (85) of retaining assembly (80). As will be described in greater detail below, pivoting lockout body (232) is configured to pivot about laterally extending pin (85) (see FIG. 6) between a locked configuration (see FIG. 15A) and an unlocked configuration (see FIGS. 15B-15C). Further, lockout body (232) is also engaged with torsion spring (86) (see FIG. 6) of retaining assembly (80) such that lockout body (232) is biased by torsion spring (86) toward the locked configuration. While lockout body (232) is pivotally attached to laterally extending pin (85) and biased by torsion spring (86) in the current example, lockout body (232) may be pivotally attached to and biased via any other suitable components as would be apparent to one skilled in the art in view of the teachings herein.

As best shown in FIG. 15A, slide block engagement protrusion (238) is configured to extend within an opening (113) defined by slide block (112) in the locked configuration. Therefore, slide block engagement protrusion (238) is configured to abut against a portion of slide block defining opening (113) to inhibit distal actuation of slide block (112)

while pivoting lockout body (232) is in the locked configuration. In the unlocked configuration, slide block engagement protrusion (238) is removed from the firing path of slide block (112), therefore allowing slide bock (112) to actuate distally in accordance with the description herein.

Similar to anvil engagement protrusion (216) described above, anvil engagement protrusion (236) of lockout body (232) is configured to contact a portion of anvil channel (60) in response to anvil half (14) reaching a suitable clamped position associated with latching pin (68) being contained within curved slots (50) of jaws (48) while clamp lever (40) is in the closed position. For example, anvil engagement protrusion (236) may be configured to contact proximal frame portion (62) of elongate anvil channel (60). Engagement between anvil engagement protrusion (236) and anvil half (14) pivots lockout body (232) about laterally extending pin (85) from the locked configuration into the unlocked configuration, to thereby allow distal actuation of firing assembly (110) in accordance with the description herein.

FIGS. 15A-15C show an illustrative use of linear surgical stapler (10") and lockout assembly (230). At the moment shown in FIG. 15A, anvil half (14) is not suitably clamped via engagement with clamp lever (40) and latching pin (68) such that lockout mechanism (230) is in the locked configuration. In such instances, anvil half (14) may be in an open position (similar to FIG. 9C); or anvil half (14) may be in a position that a user believes to be clamped, but latch pin (68) is not suitably housed within curved slots (50) of jaws (48) (similar to FIG. 10B).

As mentioned above, torsion spring (86) of retaining assembly (80) biases pivoting lockout body (232) into the locked configuration. While in the locked configuration, slide block engagement protrusion (238) is housed within opening (113) defined by slide block (112), therefore blocking distal actuation of sliding block (112). Therefore, if a user attempted to actuate firing assembly (110) in accordance with the description herein, engagement between the portion of sliding block (112) defining opening (113) and slide block engagement protrusion (238) will inhibit a user from doing so, indicating that anvil half (14) is not suitably clamped in accordance with the description herein.

FIG. 15B, shows anvil half (14) in a suitably clamped position relative to cartridge half (12) such that latch pin (68) is suitably housed within curved slots (50) of jaws (48) while clamp lever (40) is in the closed position. With anvil half (14) in the suitably clamped position, proximal frame portion (62) of elongate anvil channel (60) drives anvil engagement protrusion (236) downward, thereby pivoting lockout body (232) about laterally extending pin (85) into the unlocked configuration and compressing spring (86). In the unlocked configuration, slide block engagement protrusion (238) is pivoted out of both opening (113) and the firing path of sliding block (112).

As shown in FIG. 15C, with slide block engagement protrusion (238) pivoted out of both opening (113) and the firing path of sliding block (112), a user can actuate firing assembly (110) distally in accordance with the description herein to staple and sever tissue in accordance with description herein. Once firing assembly (110) is retracted to the pre-fired position (similar to the position shown in FIG. 15B), a user may then pivot clamp lever (40) to the open position to release tissue. Once anvil half (14) is unlatched form cartridge half (12) by pivoting clamp lever (40) from the closed position (similar to FIG. 9D) to the open position (similar to FIG. 9C), proximal frame portion (62) of elongate anvil channel (60) disengages anvil engagement protrusion (236) such that spring (86) pivots lockout body (232) back into the locked configuration as shown in FIG. 15A.

Figure 16:
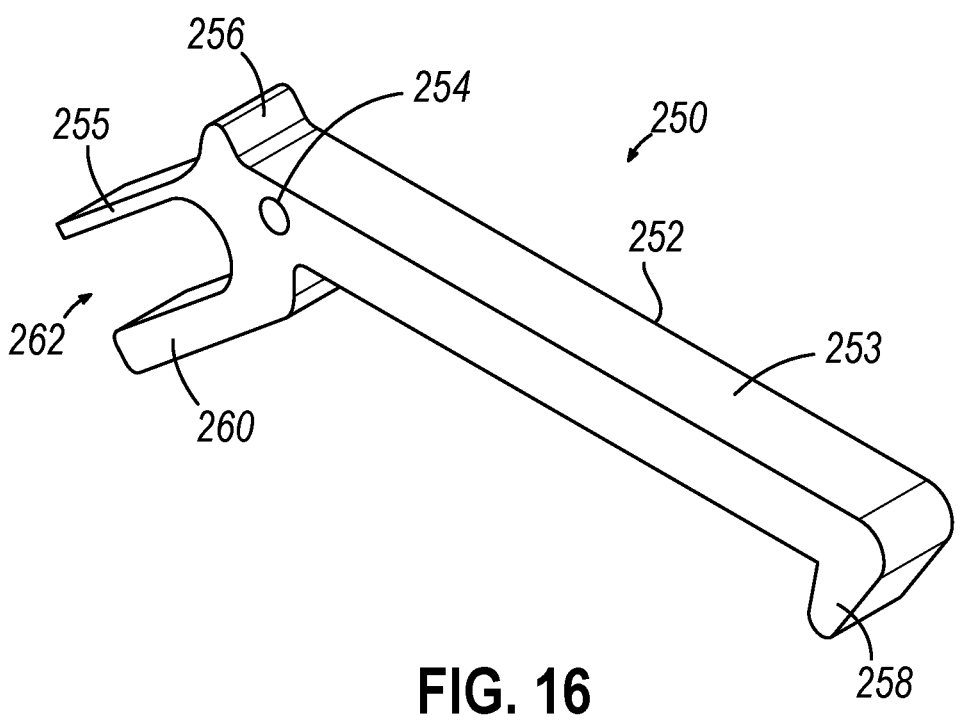
FIG. 16 depicts a perspective view of an alternative lockout body that may be readily incorporated into the linear surgical stapler of FIG. 1.
Figure 17A:
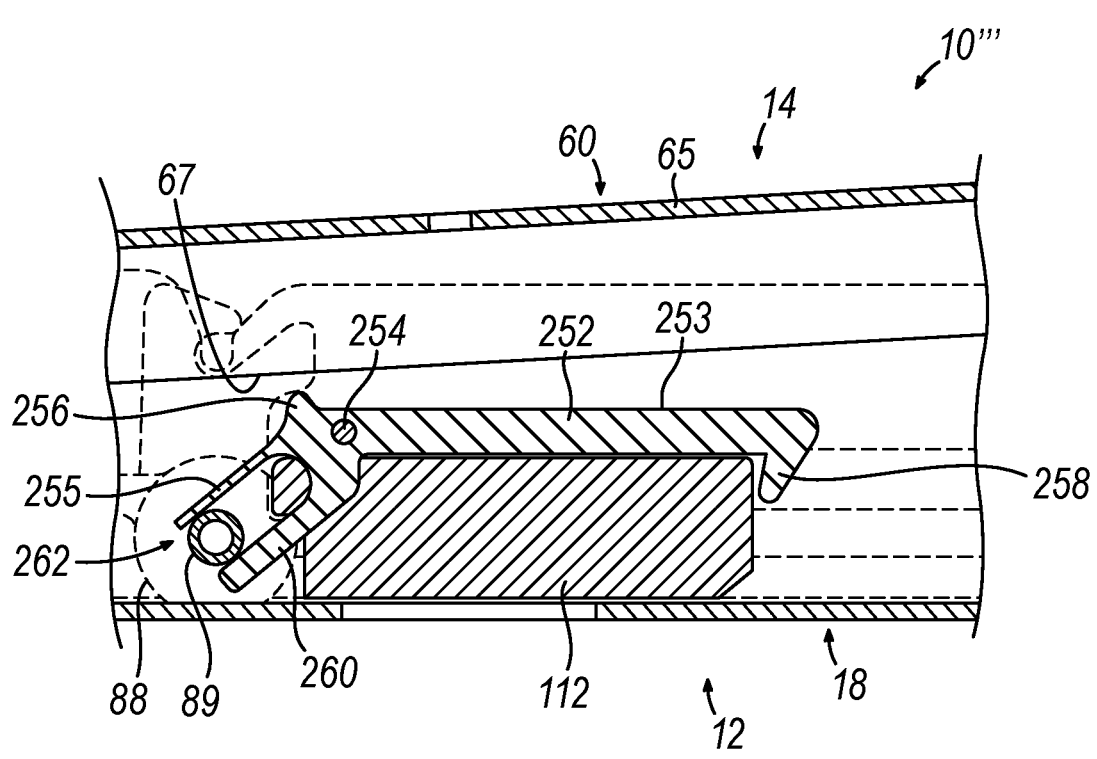
FIG. 17A depicts a cross-sectional view of a lockout assembly including the lockout body of FIG. 16 incorporated into the linear surgical stapler of FIG. 1, where the lockout assembly is in a locked configuration and the firing assembly of FIG. 5 is in a proximal, unfired position.
Figures 17B, 17C:
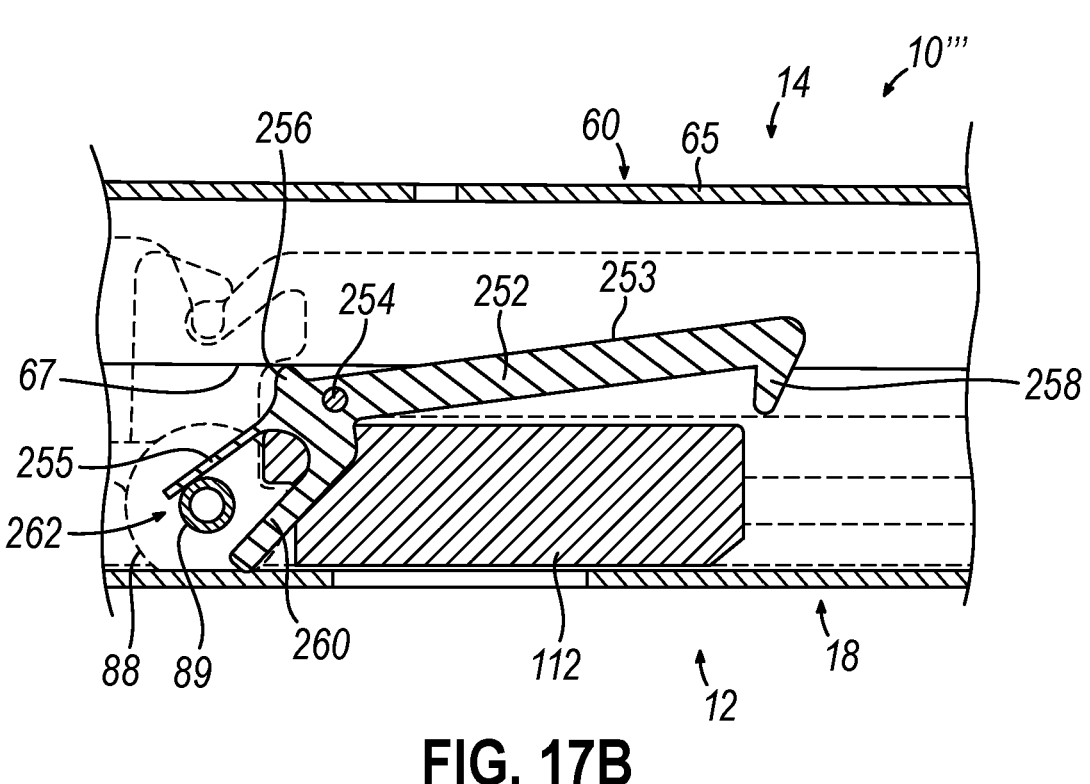
FIG. 17B depicts a sectional view of the lockout assembly of FIG. 17A incorporated into the linear surgical stapler of FIG. 1, where the lockout assembly is in an unlocked configuration and the firing assembly of FIG. 5 is in the proximal, unfired position.
FIG. 17C depicts a sectional view of the lockout assembly of FIG. 17A incorporated into the linear surgical stapler of FIG. 1, where the lockout assembly is in the unlocked configuration and the firing assembly of FIG. 5 is actuated distally toward a fired position.

FIG. 16 shows another illustrative lockout mechanism (250) that may be readily incorporated into linear stapler (10) in order to form a modified linear stapler (10'") shown in FIGS. 17A-17C. Lockout mechanism (250) is configured to function in substantially similar to lockout mechanism (200, 230) described above, with differences elaborated herein. Therefore, lockout mechanism (250) is configured to inhibit distal actuation of firing assembly (110) until distal jaw portion (64) of anvil half (14) is in a suitable clamped position relative to cartridge half (12) indicative of clamp lever (40) being both in the closed position and suitably engaged with latch pin (68) via curved slots (50) of jaws (48) (see FIG. 9D).

Lockout mechanism (250) includes a pivoting lockout body (252) having an elongated arm (253), an anvil engagement protrusion (256), a slide block engagement protrusion (258), a leaf spring (255), and a rotational stop (260). Pivoting lockout body (252) is pivotally connected to proximal frame portion (18) via a pivot pin (254). As will be described in greater detail below, pivoting lockout body (252) is configured to pivot about pin (254) between a locked configuration (see FIG. 17A) and an unlocked configuration (see FIGS. 17B-17C).

Figure 6:
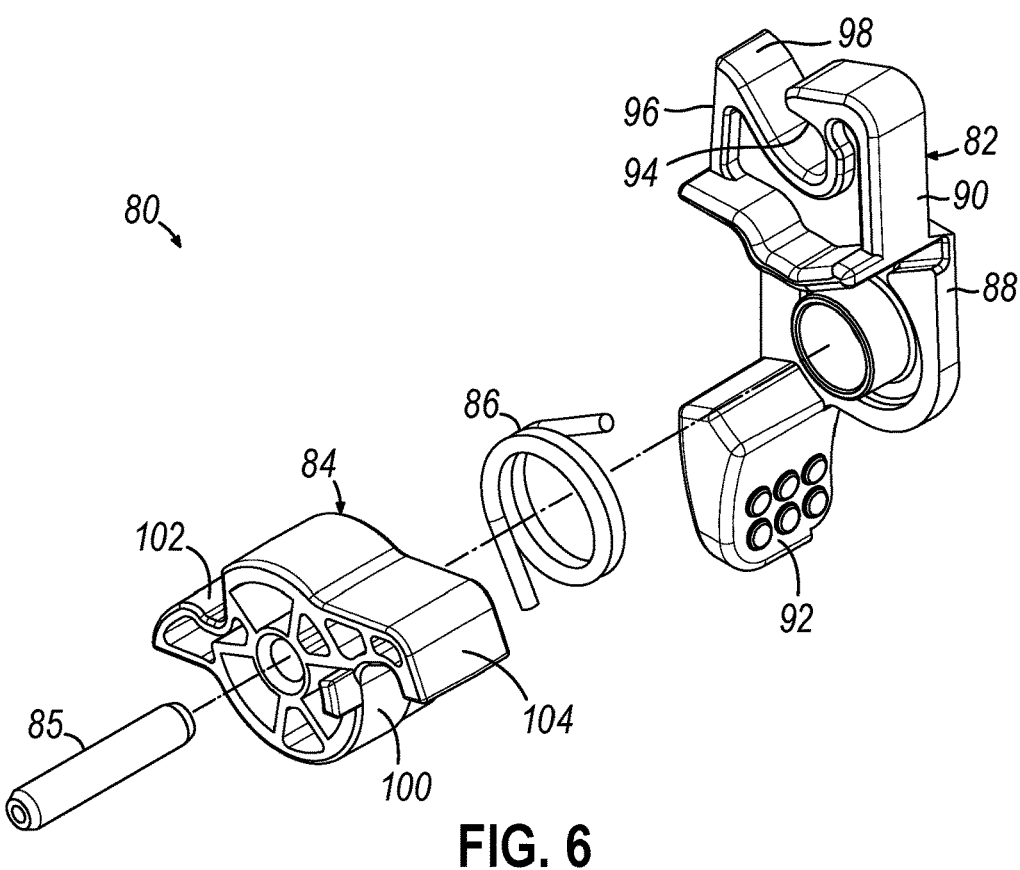
FIG. 6 depicts an exploded perspective view of the retaining assembly of FIG. 5.
Figure 7:
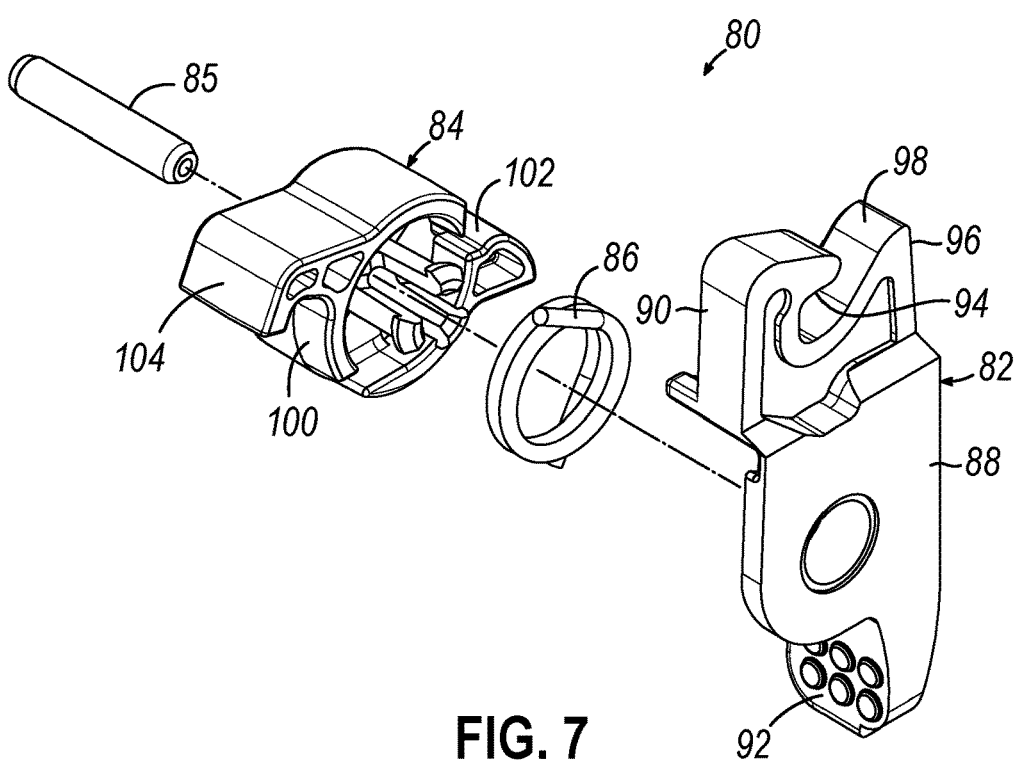
FIG. 7 depicts another exploded perspective view of the retaining assembly of FIG. 5.

Leaf spring (255) and rotational stop (260) together define a U-shaped opening (262) that is dimensioned to receive a cylindrical portion (89) of central body (88) (see FIG. 6). Leaf spring (255) engages cylindrical portion (89) of central body (88) in order to bias pivoting lockout body (252) toward the locked configuration (see FIG. 17A). Rotational stop (260) is configured to inhibit pivoting lockout body (252) from over rotating in the clockwise direction when viewed from the perspective of FIGS. 17A-17C. In other words, rotational stop (260) inhibits pivoting lockout body (252) from over rotating past the locked configuration when transitioning from the unlocked configuration (see FIG. 17B) toward the locked configuration (see FIG. 17A) in accordance with the teachings herein.

Slide block engagement protrusion (258) is located at a distal end of elongated arm (253). As best shown in FIG. 17A, slide block engagement protrusion (258) is configured to extend to a location that is directly adjacent to a distal facing surface of a pre-fired slide block (112) in the locked configuration. Therefore, slide block engagement protrusion (258) is configured to abut against a portion of slide block to inhibit distal actuation of slide block (112) while pivoting lockout body (252) is in the locked configuration. In the unlocked configuration, slide block engagement protrusion (258) is removed from the firing path of slide block (112), therefore allowing slide bock (112) to actuate distally in accordance with the description herein.

Similar to anvil engagement protrusion (216, 236) described above, anvil engagement protrusion (266) of lockout body (252) is configured to contact a portion of anvil channel (60) in response to anvil half (14) reaching a suitable clamped position associated with latching pin (68) being contained within curved slots (50) of jaws (48) while clamp lever (40) is in the closed position. For example, anvil engagement protrusion (256) of the current example is configured to contact an internal engagement surface (67) of elongate anvil channel (60). Engagement between anvil engagement protrusion (256) and internal engagement surface (67) of anvil half (14) pivots lockout body (252) about pin (254) from the locked configuration into the unlocked configuration, to thereby allow distal actuation of firing assembly (110) in accordance with the description herein.

FIGS. 17A-17C show an illustrative use of linear surgical stapler (10'") and lockout mechanism (250). At the moment shown in FIG. 17A, anvil half (14) is not suitably clamped via engagement with clamp lever (40) and latching pin (68) such that lockout mechanism (250) is in the locked configuration. In such instances, anvil half (14) may be in an open position (similar to FIG. 9C); or anvil half (14) may be in a position that a user believes to be clamped, but latch pin (68) is not suitably housed within curved slots (50) of jaws (48) (similar to FIG. 10B).

As mentioned above, leaf spring (255) engages cylindrical portion (89) of central body (88) of retaining assembly (80) in order to bias pivoting lockout body (252) into the locked configuration. While in the locked configuration, slide block engagement protrusion (258) is located adjacent to a distal surface of slide block (112) located within the firing path of slide block (112), therefore blocking distal actuation of sliding block (112). Therefore, if a user attempted to actuate firing assembly (110) in accordance with the description herein, engagement between sliding block (112) and slide block engagement protrusion (258) will inhibit a user from doing so, indicating that anvil half (14) is not suitably clamped in accordance with the description herein.

FIG. 17B, shows anvil half (14) in a suitably clamped position relative to cartridge half (12) such that latch pin (68) is suitably housed within curved slots (50) of jaws (48) while clamp lever (40) is in the closed position. With anvil half (14) in the suitably clamped position, internal engagement surface (67) of elongate anvil channel (60) drives anvil engagement protrusion (256) downward, thereby pivoting lockout body (252) about pin (254) into the unlocked configuration, thereby deflecting leaf spring (255). In the unlocked configuration, slide block engagement protrusion (258) is pivoted out of the firing path of sliding block (112).

As shown in FIG. 17C, with slide block engagement protrusion (258) pivoted out the firing path of sliding block (112), a user can actuate firing assembly (110) distally in accordance with the description herein to staple and sever tissue in accordance with description herein. Once firing assembly (110) is retracted to the pre-fired position (similar to the position shown in FIG. 17B), a user may then pivot clamp lever (40) to the open position to release tissue. Once anvil half (14) is unlatched form cartridge half (12) by pivoting clamp lever (40) from the closed position (similar to FIG. 9D) to the open position (similar to FIG. 9C), internal engagement surface (67) of elongate anvil channel (60) disengages anvil engagement protrusion (256) such that leaf spring (255) pivots lockout body (252) back into the locked configuration as shown in FIG. 17A. Rotational stop (260) also engagement cylindrical portion (89) of central body (88) in order to inhibit over rotation of pivoting lockout body (252).

II. Illustrative Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a first elongate member having a first distal portion configured to present a first stapling surface; (b) a second elongate member having a second distal portion configured to present a second stapling surface, wherein the first and second elongate members are configured to releasably couple together to enable the first and second stapling surfaces to cooperate to clamp and staple tissue with a plurality of staples; (c) a clamp lever coupled to the first elongate member, wherein the clamp lever is configured to actuate between an open position and a closed position, (d) a latch body attached to the second elongate member, wherein the clamp lever is configured to engage the latch body while actuating from the open position to the closed position to drive the first elongate member and the second elongate member from an unclamped configuration into a clamped configuration; (e) a firing assembly, wherein the firing assembly is actuatable from a home position to fire the staples into the clamped tissue; and (f) a lockout body biased toward a locked configuration and configured to actuate into an unlocked configuration, wherein the lockout body is configured to inhibit the firing assembly from actuating away from the home position in the locked configuration, wherein the lockout body is configured to permit the firing assembly to actuate away from the home position in the unlocked configuration, wherein the lockout body is configured to actuate into the unlocked configuration in response to the clamp lever actuating into the closed position while engaged with the latch body, wherein the lockout body is configured to remain in the locked configuration in response to the clamp lever actuating into the closed position while disengaged with the latch body.

Example 2

The apparatus of Example 1, wherein the lockout body is pivotally coupled to the first elongate member via a pin.

Example 3

The apparatus of Example 2, wherein the lockout body comprises a lockout protrusion and a rotation protrusion, wherein the lockout protrusion is configured to inhibit the firing assembly from actuating away from the home position in the locked configuration, wherein the rotation protrusion is configured to engage the second elongate member to thereby pivot the lockout body into the unlocked configuration.

Example 4

The apparatus of Example 3, further comprising a spring biasing the lockout body into the locked configuration.

Example 5

The apparatus of Example 4, wherein the spring comprises a compression spring interposed between the lockout body and the first elongate member.

Example 6

The apparatus of Example 4, wherein the spring comprises a torsion spring disposed around the pin.

Example 7

The apparatus of Example 4, wherein the spring comprise a leaf spring integrated into the lockout body.

Example 8

The apparatus of Example 7, wherein the leaf spring extends proximally from the rotation protrusion.

Example 9

The apparatus of Example 8, wherein the lockout body further comprises a rotational stop, wherein the leaf spring and the rotational stop define an opening housing a portion of the first elongate member, wherein the leaf spring is configured to engage the portion of the first elongated member to bias the locking body into the locked configuration.

Example 10

The apparatus of Example 9, wherein the rotational stop is configured to engage the portion of the first elongate member to inhibit over rotation of the lockout body.

Example 11

The apparatus of any one or more of the preceding Examples, wherein the firing assembly comprises a slide block housed within the first elongate member, wherein the lockout body is configured to directly engage the slide block in the locked configuration.

Example 12

The apparatus of Example 11, wherein the first elongate member comprises a cartridge channel, wherein the second elongate member comprises an anvil channel.

Example 13

The apparatus of either one or more of Examples 11 or 12, wherein the slide block defines an opening, wherein the lockout body comprises a projection configured to fit within the opening in the locked configuration.

Example 14

The apparatus of any one or more of the preceding Examples, wherein the first elongate member and the second elongate member configured to releasably couple at a proximal end.

Example 15

The apparatus of any one or more of the preceding Examples, wherein the clamp lever is pivotally coupled to the first elongate body.

Example 16

An apparatus comprising: (a) a first elongate member having a distal portion configured to present a first stapling surface; (b) a second elongate member having a distal portion configured to present a second stapling surface, the second elongate member further comprising a latch pin, wherein the first and second elongate members are configured to releasably couple together at their proximal ends to enable the first and second stapling surfaces to cooperate to clamp and staple tissue with a plurality of staples; (c) a clamp member pivotally coupled to the first elongate member, wherein the clamp member is movable relative to the first and second elongate members from an open position to a closed position while engaging the latch pin drive the first elongate member and the second elongate member from an unclamped configuration into a clamped configuration; and (d) a lockout body configured inhibit stapling of tissue in a biased locked configuration and allow stapling of tissue in an unlocked configuration, wherein the lockout body is configured to transition between the biased locked configuration and the unlocked configuration in response to the clamp member reaching the closed position while engaged with the latch pin, wherein the lockout body is configured to remain in the biased locked configuration in response to the clamp member reaching the closed position while disengaged with the latch pin.

Example 17

The apparatus of Example 16, wherein the lockout body is pivotally attached to the first elongate member via a pin.

Example 18

The apparatus of either Example 16 or 17, further comprising a firing assembly associated with the first elongate member, wherein the firing assembly is configured to actuate distally along the first elongate member in order to staple tissue.

Example 19

The apparatus of Example 18, wherein the lockout body is configured to directly engage a firing block of the firing assembly in the locked configuration.

Example 20

An apparatus comprising: (a) an cartridge channel having a first distal portion configured to present a first stapling surface; (b) a anvil channel having a second distal portion configured to present a second stapling surface, wherein the cartridge channel and the anvil channel are configured to releasably couple together to enable the first and second stapling surfaces to cooperate to clamp and staple tissue with a plurality of staples; (c) a clamp lever coupled to the cartridge channel, wherein the clamp lever is configured to actuate between an open position and a closed position, (d) an anvil latch pin attached to the anvil channel, wherein the clamp lever is configured to engage the anvil latch pin while actuating from the open position to the closed position to drive the cartridge channel and the anvil channel from an unclamped configuration into a clamped configuration; (e) a firing assembly, wherein the firing assembly is actuatable from a home position to fire the staples into the clamped tissue; and (d) a lockout body configured inhibit stapling of tissue in a biased locked configuration and allow stapling of tissue in an unlocked configuration, wherein the lockout body is configured to transition between the biased locked configuration and the unlocked configuration in response to the clamp lever reaching the closed position while engaged with the anvil latch pin, wherein the lockout body is configured to remain in the biased locked configuration in response to the clamp lever reaching the closed position while disengaged with the anvil latch pin.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more teachings disclosed herein may be combined with any one or more teachings disclosed in U.S. Pat. No. 10,631,866, entitled "Release Mechanism for Linear Surgical Stapler," issued Apr. 28, 2020; U.S. Pat. No. 10,667,818, entitled "Lockout Assembly for Linear Surgical Stapler," issued Jun. 2, 2020; U.S. Pat. No. 10,932,781, entitled "Features to Align and Close Linear Surgical Stapler," issued Mar. 2, 2021; U.S. Pat. No. 10,898,197, entitled "Releasable Coupling Features for Proximal Portions of Linear Surgical Stapler," issued Jan. 26, 2021; U.S. Pat. No. 10,874,398, entitled "Firing Lever Assembly for Linear Surgical Stapler," issued Dec. 29, 2020; U.S. Pat. No. 10,687,819, entitled "Clamping Mechanism for Linear Surgical Stapler," issued Jun. 23, 2020; U.S. Pat. No. 10,898,187, entitled "Firing System for Linear Surgical Stapler," issued Jan. 26, 2021; U.S. Pat. No. 11,033,266, entitled "Decoupling Mechanism for Linear Surgical Stapler, issued Jun. 15, 2021; U.S. Pat. No. 11,045,193, entitled "Anvil Assembly for Linear Surgical Stapler," issued Jun. 29, 2021; U.S. Pat. No. 10,905,419, entitled "Closure Assembly for Linear Surgical Stapler," issued Feb. 2, 2021; U.S. Pat. No. 11,278,285, entitled "Clamping Assembly for Linear Surgical Stapler," issued Mar. 22, 2022; U.S. Pat. No. 11,229,433, entitled "Linear Surgical Stapler," issued Jan. 25, 2022; U.S. Pub. No. 2022/0142641, entitled "System and Method for Forming Pockets in Anvil of Surgical Stapler," published May 12, 2022, issued as U.S. Pat. No. 12,016,555 on Jun. 25, 2024; U.S. Pat. No. 11,224,425, entitled "Surgical Linear Cutter Wishbone Separation Mechanism with Detent," issued Jan. 18, 2022; U.S. Pat. No. 11,219,454, entitled "Pin Trap Mechanism for Surgical Linear Cutter," issued Jan. 11, 2022; U.S. Pub. No. 2021/0369272, entitled "Separation Mechanism for Surgical Linear Cutter," published Dec. 2, 2021 and issued as U.S. Pat. No. 11,399,827 on Aug. 2, 2022; U.S. patent application Ser. No. 17/489,879, entitled "Lockout Feature for Linear Surgical Stapler Cartridge," filed Sep. 30, 2021 and issued as U.S. Pat. No. 11,937,812 on Mar. 26, 2024; U.S. patent application Ser. No. 29/842,580, entitled "Staple Cartridge for Linear Surgical Stapler," filed Jun. 16, 2022, issued as U.S. Design Pat. No. D1,067,431 on Mar. 18, 2025; and/or U.S. patent application Ser. No. 29/842,581, entitled "Linear Surgical Stapler," filed Jun. 16, 2022. The disclosure of each of these references is incorporated by reference herein, in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
(a) a first elongate body having a first distal portion configured to present a first stapling surface;

(b) a second elongate body having a second distal portion configured to present a second stapling surface, wherein the first and second elongate body are configured to releasably couple together to enable the first and second stapling surfaces to cooperate to clamp and staple tissue with a plurality of staples;
(c) a clamp lever coupled to the first elongate body, wherein the clamp lever is configured to actuate between an open position and a closed position,
(d) a latch body attached to the second elongate body, wherein the clamp lever is configured to engage the latch body while actuating from the open position to the closed position to drive the first elongate body and the second elongate body from an unclamped configuration into a clamped configuration;
(e) a firing assembly, wherein the firing assembly is actuatable from a home position to fire the staples into the clamped tissue; and
(f) a lockout body biased toward a locked configuration and configured to actuate into an unlocked configuration,
wherein the lockout body is configured to inhibit the firing assembly from actuating away from the home position in the locked configuration,
wherein the lockout body is configured to permit the firing assembly to actuate away from the home position in the unlocked configuration,
wherein the lockout body is configured to actuate into the unlocked configuration in response to the clamp lever actuating into the closed position while engaged with the latch body,
wherein the lockout body is configured to remain in the locked configuration in response to the clamp lever actuating into the closed position while disengaged with the latch body,
wherein the lockout body is pivotally coupled to the first elongate body via a pin.

2. The apparatus of claim 1, wherein the lockout body comprises a lockout protrusion and a rotation protrusion, wherein the lockout protrusion is configured to inhibit the firing assembly from actuating away from the home position in the locked configuration, wherein the rotation protrusion is configured to engage the second elongate body to thereby pivot the lockout body into the unlocked configuration.

3. The apparatus of claim 2, further comprising a spring biasing the lockout body into the locked configuration.

4. The apparatus of claim 3, wherein the spring comprises a compression spring interposed between the lockout body and the first elongate body.

5. The apparatus of claim 3, wherein the spring comprises a torsion spring disposed around the pin.

6. The apparatus of claim 3, wherein the spring comprise a leaf spring integrated into the lockout body.

7. The apparatus of claim 6, wherein the leaf spring extends proximally from the rotation protrusion.

8. The apparatus of claim 7, wherein the lockout body further comprises a rotational stop, wherein the leaf spring and the rotational stop define an opening housing a portion of the first elongate body, wherein the leaf spring is configured to engage the portion of the first elongated body to bias the locking body into the locked configuration.

9. The apparatus of claim 8, wherein the rotational stop is configured to engage the portion of the first elongate body to inhibit over rotation of the lockout body.

10. The apparatus of claim 1, wherein the firing assembly comprises a slide block housed within the first elongate body, wherein the lockout body is configured to directly engage the slide block in the locked configuration.

11. The apparatus of claim 10, wherein the first elongate body comprises a cartridge channel, wherein the second elongate body comprises an anvil channel.

12. The apparatus of claim 10, wherein the slide block defines an opening, wherein the lockout body comprises a projection configured to fit within the opening in the locked configuration.

13. The apparatus of claim 1, wherein the first elongate body and the second elongate body configured to releasably couple at a proximal end.

14. The apparatus of claim 1, wherein the clamp lever is pivotally coupled to the first elongate body.

15. An apparatus comprising:

(a) a first elongate body having a distal portion configured to present a first stapling surface;

(b) a second elongate body having a distal portion configured to present a second stapling surface, the second elongate body further comprising a latch pin, wherein the first and second elongate bodies are configured to releasably couple together at their proximal ends to enable the first and second stapling surfaces to cooperate to clamp and staple tissue with a plurality of staples;

(c) a clamp body pivotally coupled to the first elongate body, wherein the clamp lever is movable relative to the first and second elongate bodies from an open position to a closed position while engaging the latch pin drive the first elongate body and the second elongate body from an unclamped configuration into a clamped configuration; and (d) a lockout body configured inhibit stapling of tissue in a biased locked configuration and allow stapling of tissue in an unlocked configuration, wherein the lockout body is configured to transition between the biased locked configuration and the unlocked configuration in response to the clamp lever reaching the closed position while engaged with the latch pin, wherein the lockout body is configured to remain in the biased locked configuration in response to the clamp body reaching the closed position while disengaged with the latch pin, wherein the lockout body is pivotally attached to the first elongate body via a pin.

16. The apparatus of claim 15, further comprising a firing assembly associated with the first elongate body, wherein the firing assembly is configured to actuate distally along the first elongate body in order to staple tissue.

17. The apparatus of claim 16, wherein the lockout body is configured to directly engage a firing block of the firing assembly in the locked configuration.

18. An apparatus comprising:

(a) a cartridge channel having a first distal portion configured to present a first stapling surface;

(b) an anvil channel having a second distal portion configured to present a second stapling surface, wherein the cartridge channel and the anvil channel are configured to releasably couple together to enable the first and second stapling surfaces to cooperate to clamp and staple tissue with a plurality of staples;

(c) a clamp lever coupled to the cartridge channel, wherein the clamp lever is configured to actuate between an open position and a closed position, (d) an anvil latch pin attached to the anvil channel, wherein the clamp lever is configured to engage the anvil latch pin while actuating from the open position to the closed position to drive the cartridge channel and the anvil channel from an unclamped configuration into a clamped configuration;

(e) a firing assembly, wherein the firing assembly is actuatable from a home position to fire the staples into the clamped tissue; and (d) a lockout body configured inhibit stapling of tissue in a biased locked configuration and allow stapling of tissue in an unlocked configuration, wherein a portion of the anvil channel is configured to drive the lockout body into the unlocked configuration, wherein the lockout body is configured to transition between the biased locked configuration and the unlocked configuration in response to the clamp lever reaching the closed position while engaged with the anvil latch pin, wherein the lockout body is configured to remain in the biased locked configuration in response to the clamp lever reaching the closed position while disengaged with the anvil latch pin.

\* \* \* \* \*